United States Patent
Cosgrove et al.

(10) Patent No.: US 6,962,605 B2
(45) Date of Patent: Nov. 8, 2005

(54) MINIMALLY-INVASIVE ANNULOPLASTY REPAIR SEGMENT DELIVERY TEMPLATE AND SYSTEM

(75) Inventors: Delos M. Cosgrove, Hunting Valley, OH (US); Stefan G. Schreck, Vista, CA (US); Richard S. Rhee, Diamond Bar, CA (US)

(73) Assignee: Edwards Lifesciences Corporation, Irvine, CA (US)

(*) Notice: Subject to any disclaimer, the term of this patent is extended or adjusted under 35 U.S.C. 154(b) by 0 days.

(21) Appl. No.: 10/351,036

(22) Filed: Jan. 24, 2003

(65) Prior Publication Data

US 2003/0144732 A1 Jul. 31, 2003

Related U.S. Application Data

(63) Continuation of application No. 09/680,202, filed on Oct. 5, 2000, now Pat. No. 6,602,288.

(51) Int. Cl.[7] .................................................. A61F 2/24
(52) U.S. Cl. ...................................... 623/2.36; 623/2.11
(58) Field of Search ............................. 623/2.36–2.38, 623/2.11

(56) References Cited

U.S. PATENT DOCUMENTS

| | | |
|---|---|---|
| 4,164,046 A | 8/1979 | Cooley |
| 4,679,556 A | 7/1987 | Lubock et al. |
| 4,850,358 A | 7/1989 | Millar |
| 4,917,698 A | 4/1990 | Carpentier et al. |
| 5,041,130 A | 8/1991 | Cosgrove et al. |
| 5,061,277 A | 10/1991 | Carpentier et al. |
| 5,064,431 A | 11/1991 | Gilbertson et al. |
| 5,104,407 A | 4/1992 | Lam et al. |
| 5,201,880 A | 4/1993 | Wright et al. |
| 5,290,300 A | 3/1994 | Cosgrove et al. |
| 5,350,420 A | 9/1994 | Cosgrove et al. |
| 5,360,014 A | 11/1994 | Sauter et al. |
| 5,403,305 A | 4/1995 | Sauter et al. |
| 5,476,510 A | 12/1995 | Eberhardt et al. |
| 5,489,296 A | 2/1996 | Love et al. |
| 5,531,785 A | 7/1996 | Love et al. |
| 5,560,487 A | 10/1996 | Starr |
| 5,716,397 A | 2/1998 | Myers |
| 5,843,177 A | 12/1998 | Vanney et al. |

(Continued)

FOREIGN PATENT DOCUMENTS

| | | |
|---|---|---|
| EP | 0 804 911 | 11/1997 |
| FR | 2 799 364 A1 | 4/2001 |
| WO | WO 01/26586 | 4/2001 |
| WO | WO 02/28321 A3 | 4/2002 |
| WO | WO 02/28321 A2 | 4/2002 |

Primary Examiner—Alvin J. Stewart
(74) Attorney, Agent, or Firm—Guy L. Cumberbatch; Debra D. Condino

(57) ABSTRACT

An annuloplasty repair segment and template for heart valve annulus repair. The elongate flexible template may form a distal part of a holder that also has a proximal handle. Alternatively, the template may be releasably attached to a mandrel that slides within a delivery sheath, the template being released from the end of the sheath to enable manipulation by a surgeon. A tether connecting the template and mandrel may also be provided. The template may be elastic, temperature responsive, or multiple linked segments. The template may be aligned with the handle and form a two- or three-dimensional curve out of alignment with the handle such that the annuloplasty repair segment attached thereto conforms to the curve. The template may be actively or passively converted between its straight and curved positions. The combined holder and ring is especially suited for minimally-invasive surgeries in which the combination is delivered to an implantation site through a small access incision with or without a cannula, or through a catheter passed though the patient's vasculature.

13 Claims, 14 Drawing Sheets

U.S. PATENT DOCUMENTS

| | | | |
|---|---|---|---|
| 5,961,539 A | 10/1999 | Northrup, III et al. | |
| 5,972,030 A | 10/1999 | Garrison et al. | |
| 6,093,184 A | 7/2000 | Campbell et al. | |
| 6,159,240 A | 12/2000 | Sparer et al. | |
| 6,210,432 B1 * | 4/2001 | Solem et al. | 623/1.15 |
| 6,231,601 B1 | 5/2001 | Myers et al. | |
| 6,250,308 B1 | 6/2001 | Cox | |
| 6,287,339 B1 * | 9/2001 | Vazquez et al. | 623/2.4 |
| 6,350,281 B1 * | 2/2002 | Rhee | 623/2.11 |
| 6,368,348 B1 * | 4/2002 | Gabbay | 623/2.36 |
| 6,406,492 B1 * | 6/2002 | Lytle | 623/2.11 |
| 6,419,696 B1 * | 7/2002 | Ortiz et al. | 623/2.37 |
| 6,425,916 B1 * | 7/2002 | Garrison et al. | 623/2.11 |
| 6,524,338 B1 * | 2/2003 | Gundry | 623/2.11 |
| 6,537,314 B2 * | 3/2003 | Langberg et al. | 623/2.36 |
| 6,569,198 B1 * | 5/2003 | Wilson et al. | 623/2.37 |
| 6,613,085 B1 * | 9/2003 | Anderson et al. | 623/2.11 |
| 6,676,702 B2 * | 1/2004 | Mathis | 623/2.36 |
| 6,689,164 B1 * | 2/2004 | Seguin | 623/2.36 |
| 6,800,090 B2 * | 10/2004 | Alferness et al. | 623/2.36 |

* cited by examiner

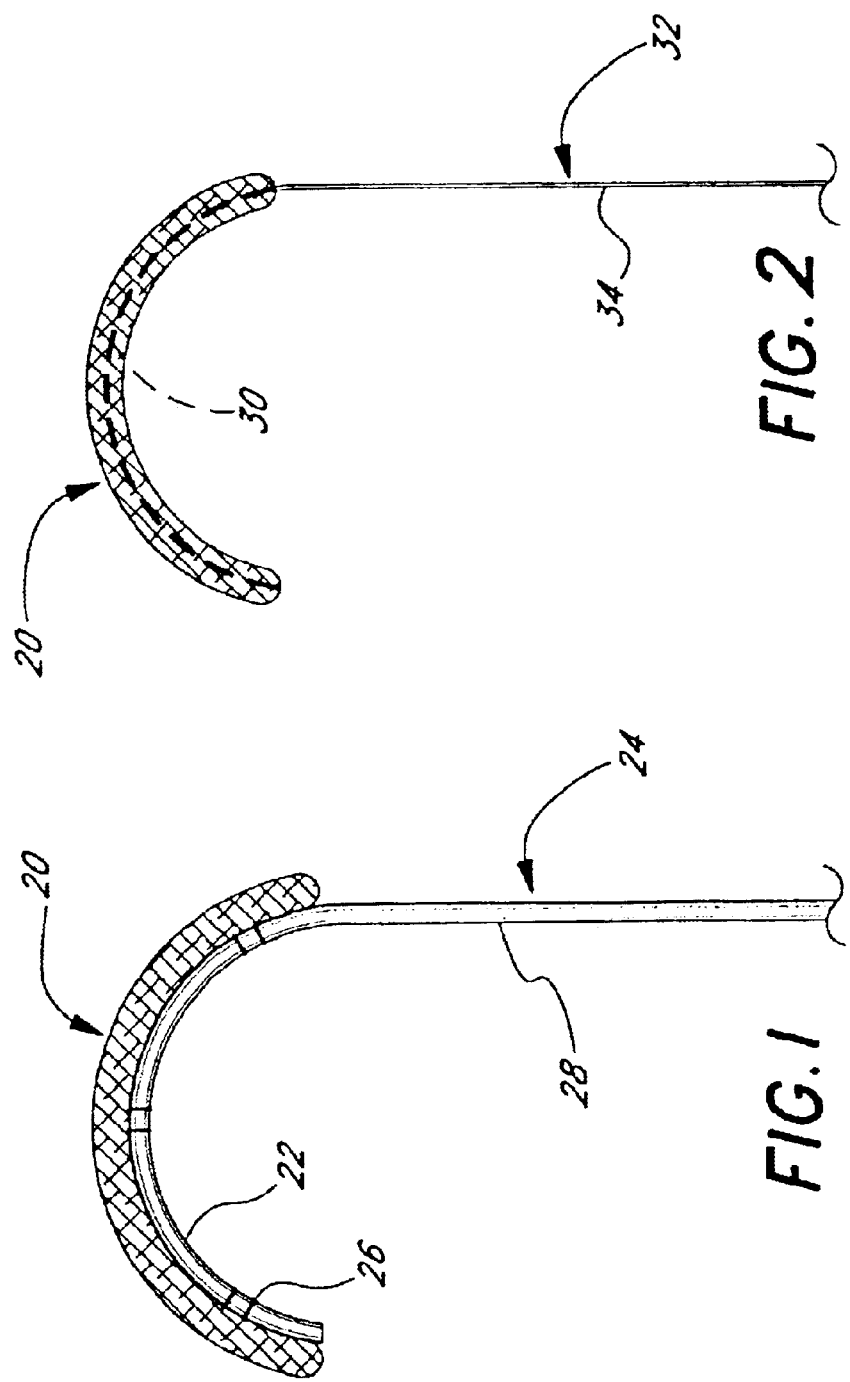

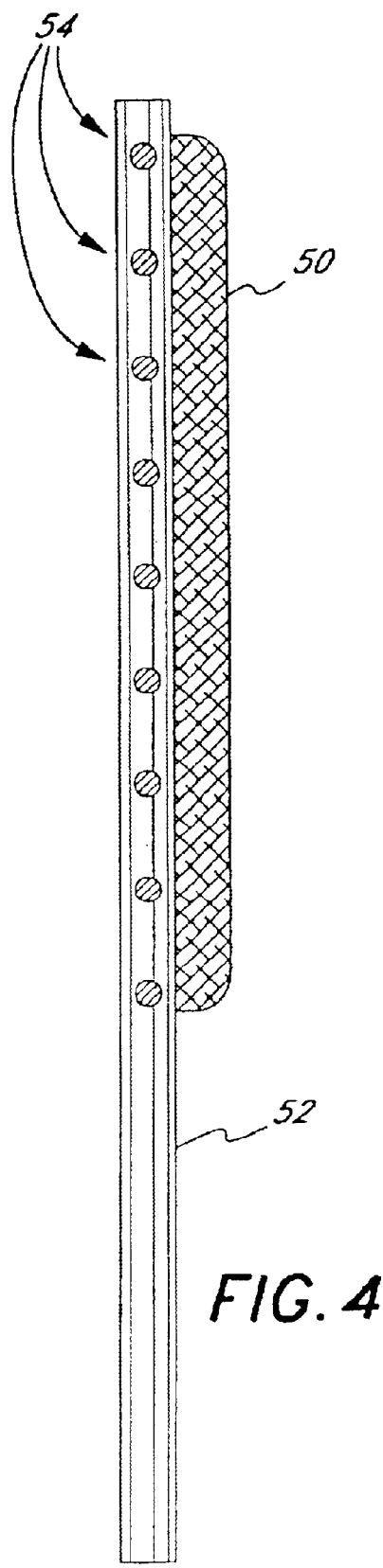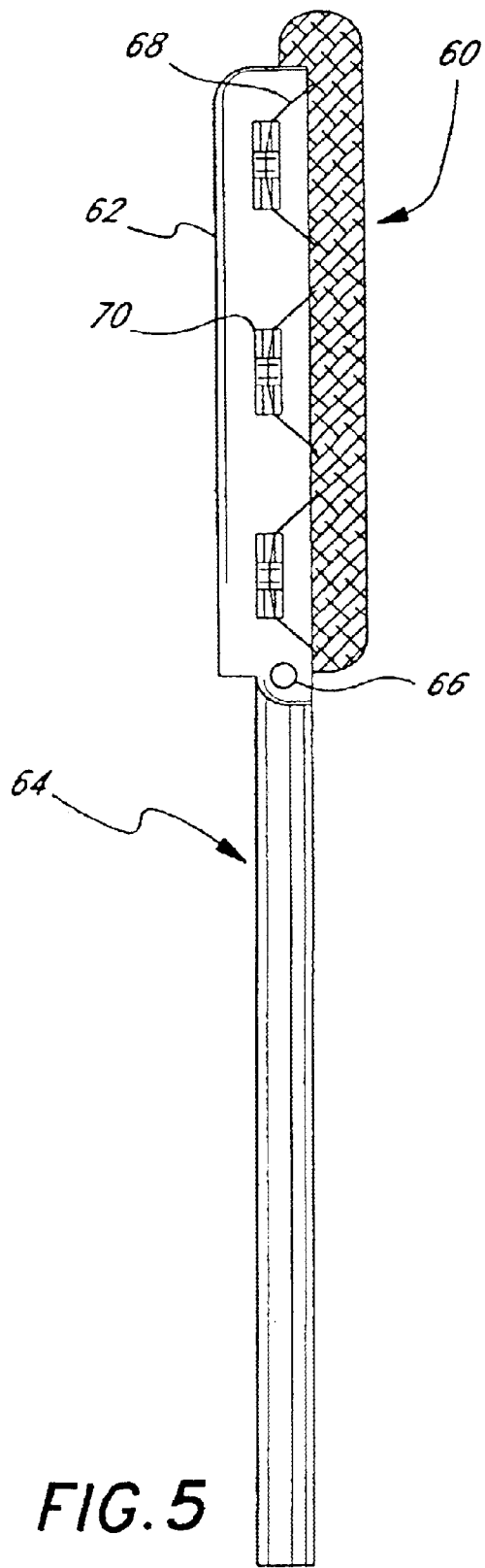
FIG. 4
FIG. 5

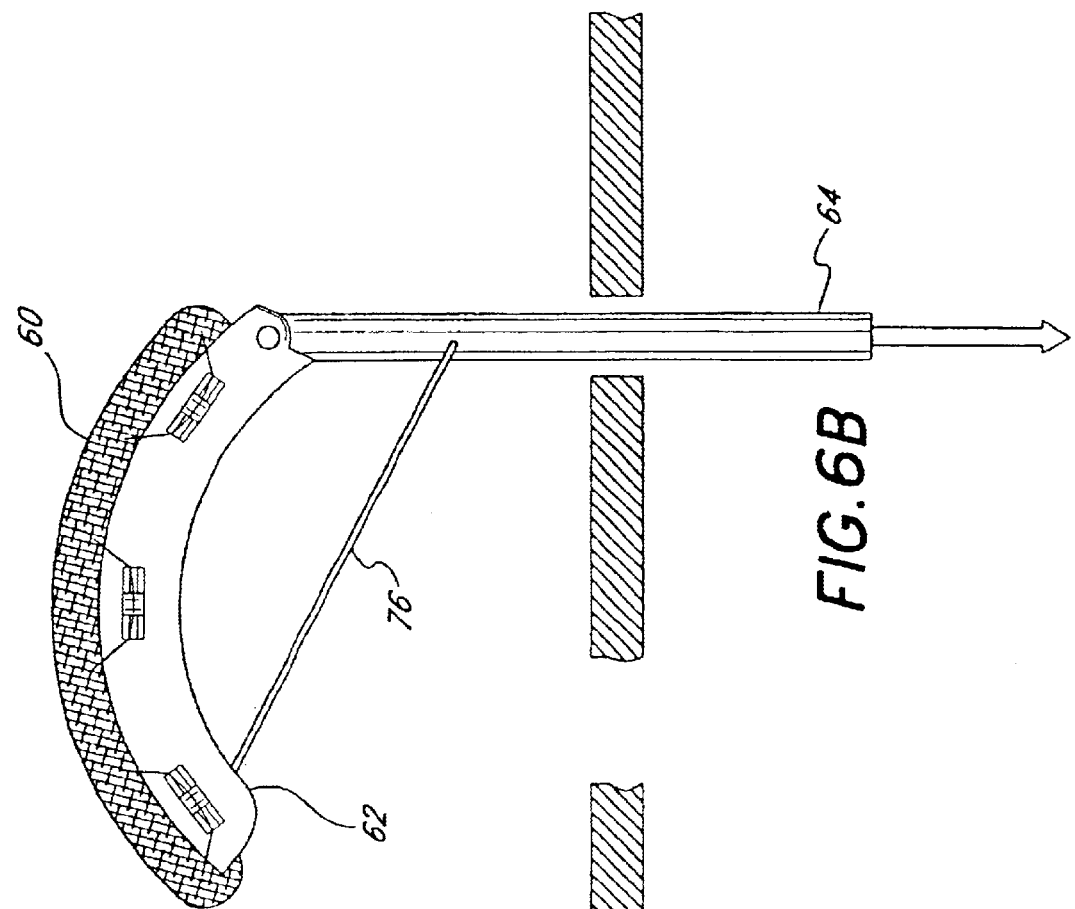
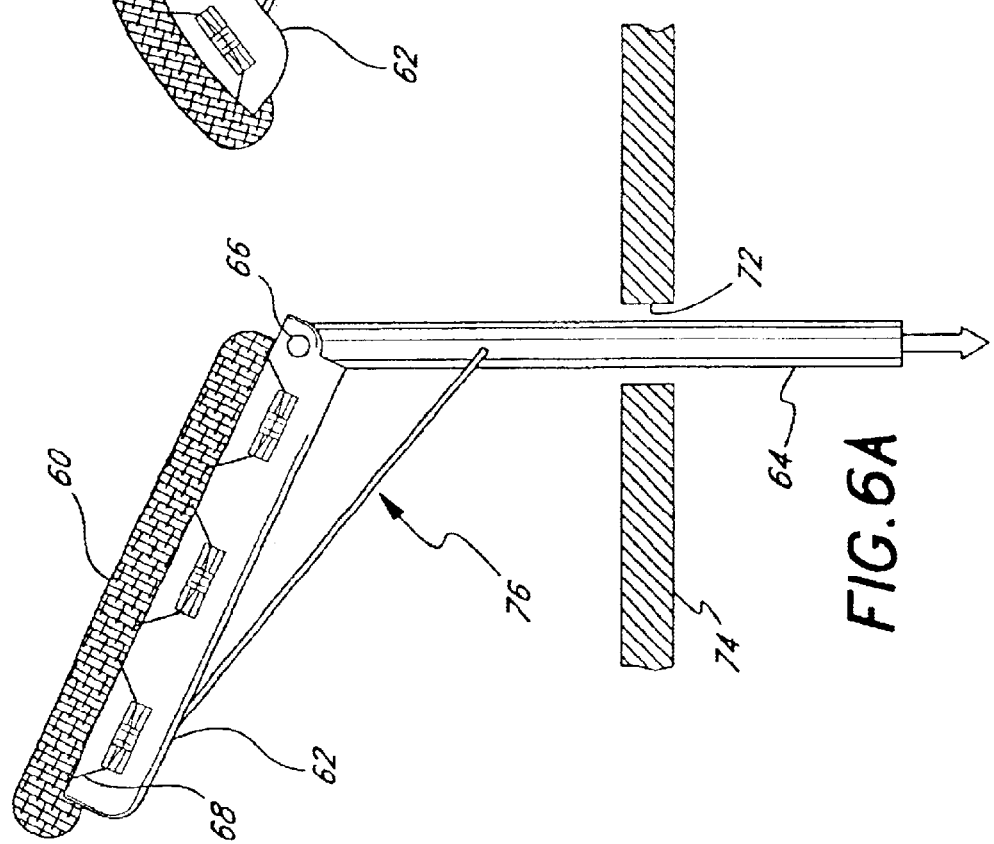

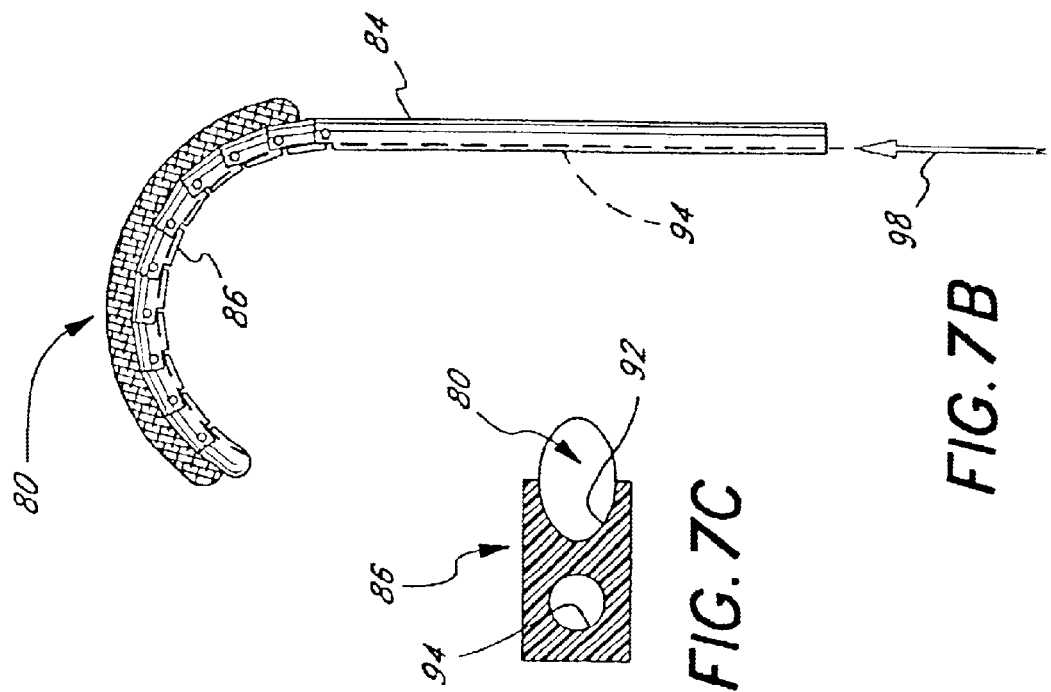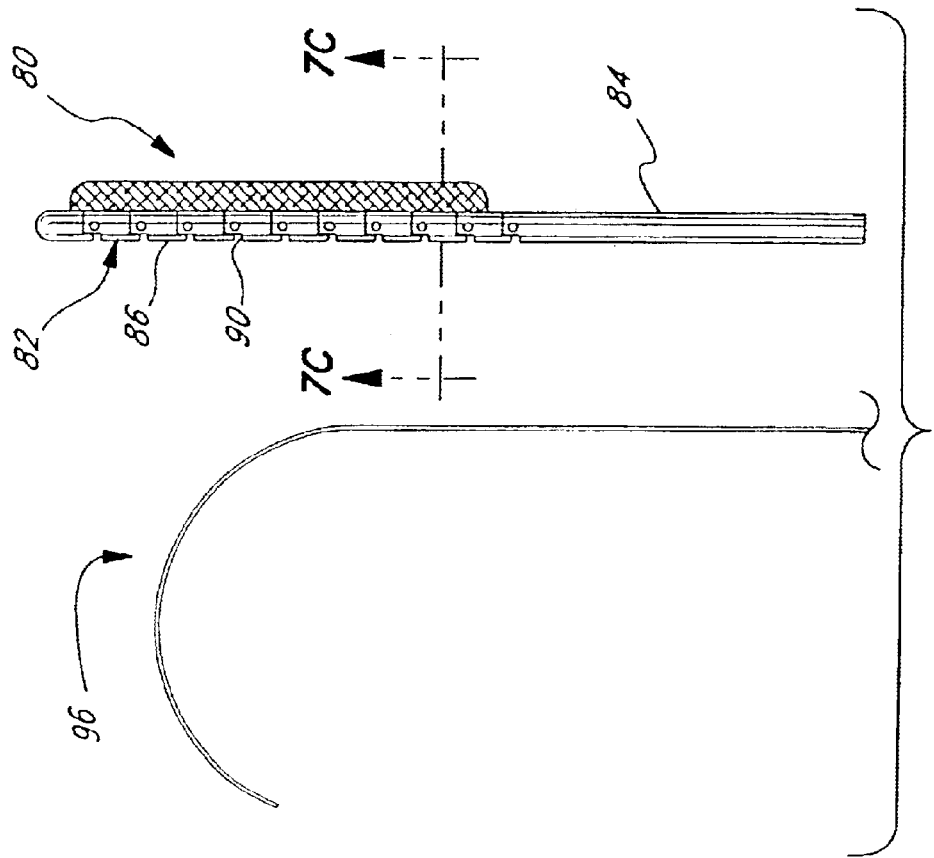

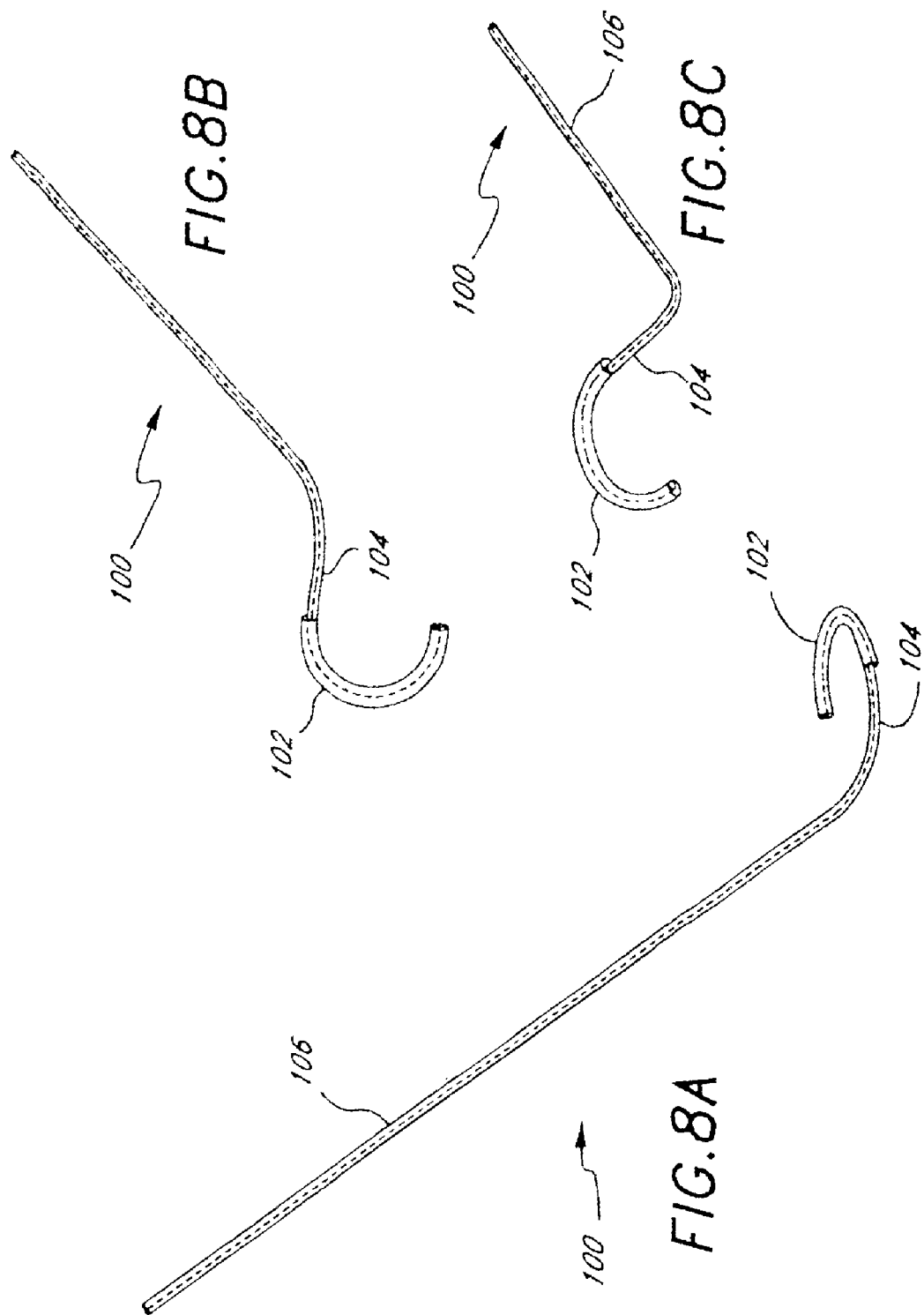

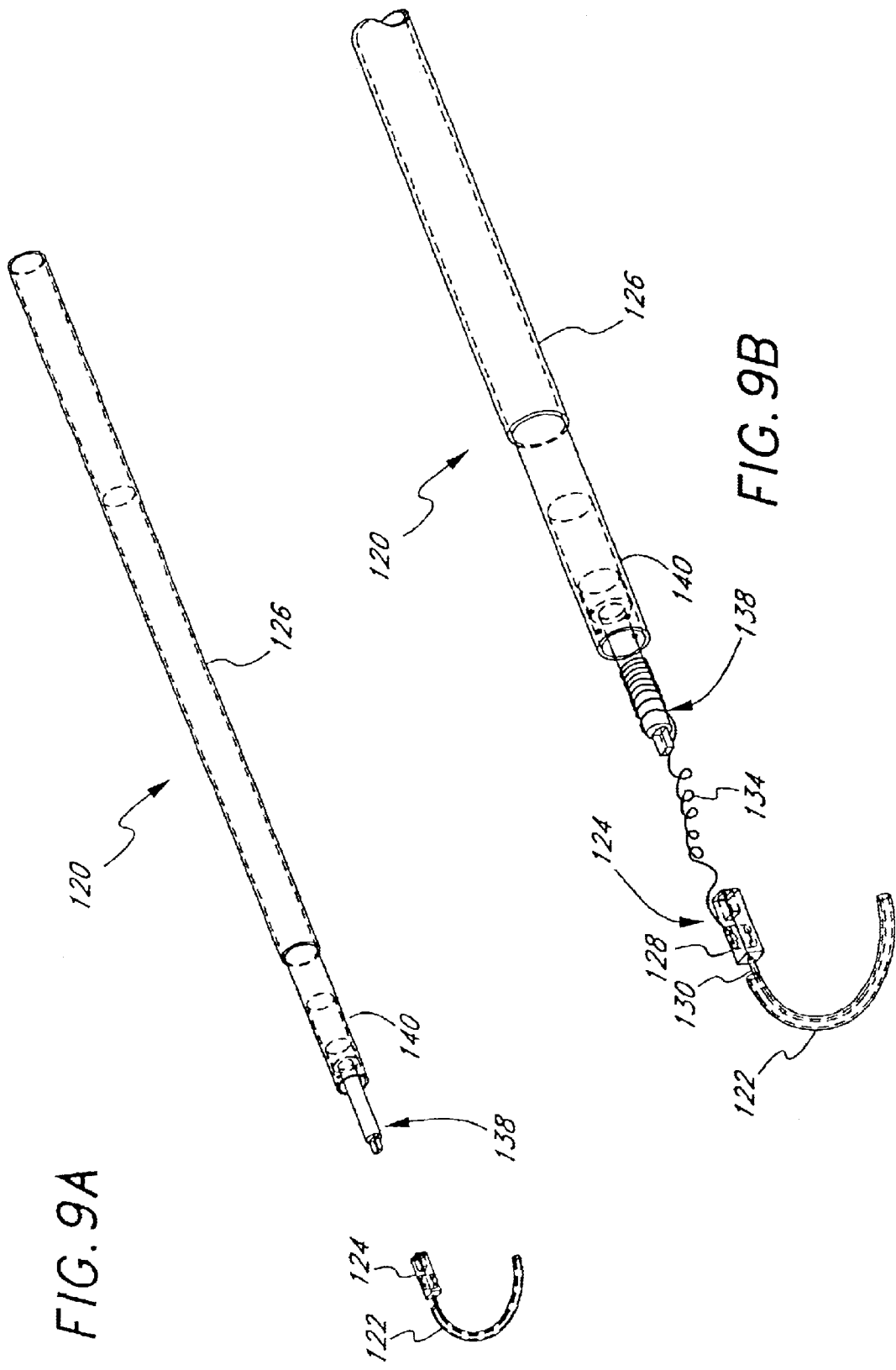

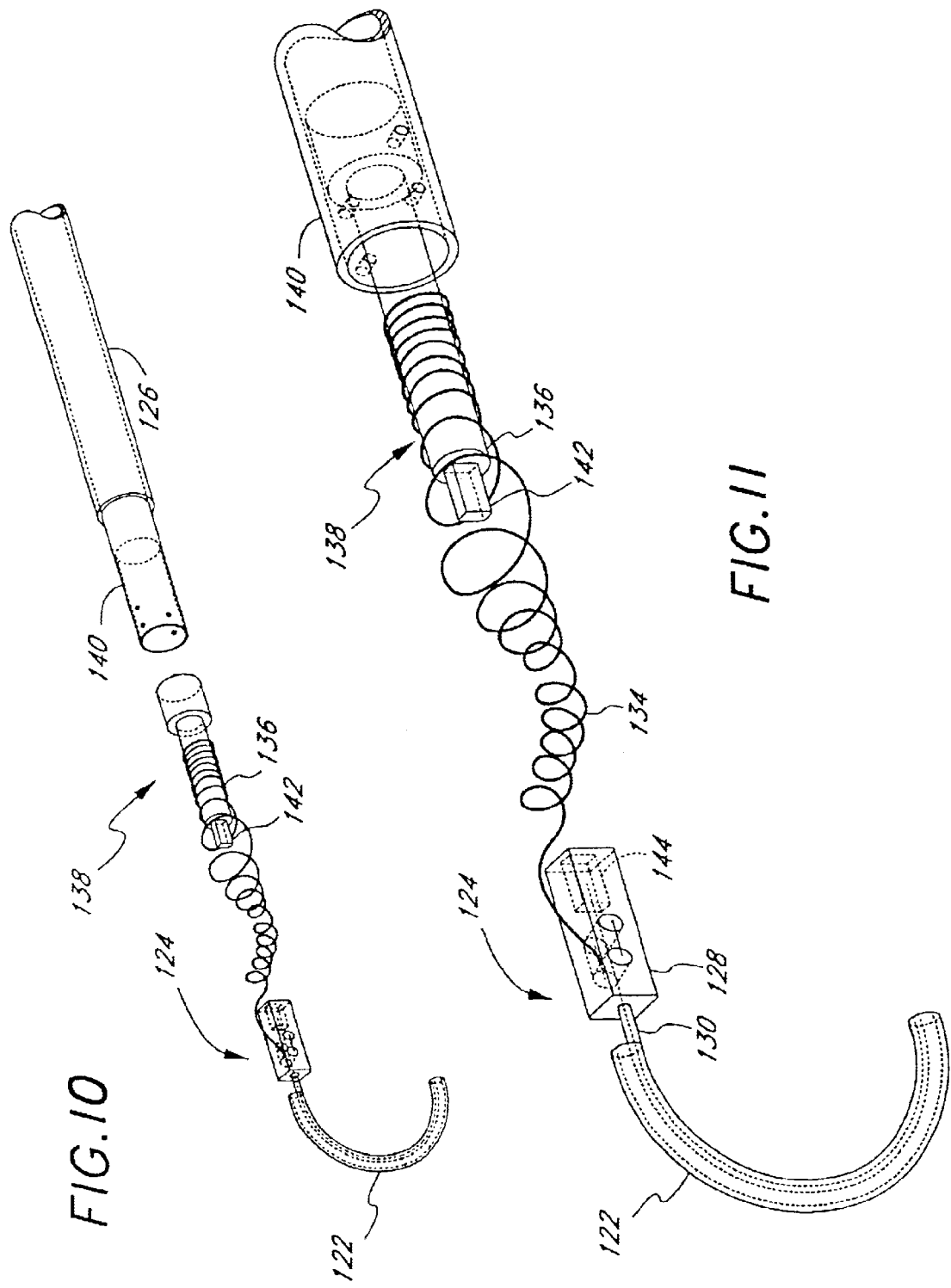

MINIMALLY-INVASIVE ANNULOPLASTY REPAIR SEGMENT DELIVERY TEMPLATE AND SYSTEM

RELATED APPLICATIONS

The present application claims priority as a continuation from U.S. application Ser. No. 09/680,202, filed Oct. 5, 2000, now issued as U.S. Pat. No. 6,602,288.

FIELD OF THE INVENTION

The present invention relates generally to medical devices and particularly to a template for delivering annuloplasty repair segments or rings especially for use in minimally-invasive surgeries.

BACKGROUND OF THE INVENTION

Prosthetic annuloplasty rings are used to repair or reconstruct damaged or diseased heart valve annuluses. In vertebrate animals, the heart is a hollow muscular organ having four pumping chambers: the left and right atria and the left and right ventricles, each provided with its own one-way valve. The natural heart valves are identified as the aortic, mitral (or bicuspid), tricuspid and pulmonary valves. The valves of the heart separate chambers therein, and are each mounted in an annulus therebetween. The annuluses comprise dense fibrous rings attached either directly or indirectly to the atrial and ventricular muscle fibers.

Heart valve disease is a widespread condition in which one or more of the valves of the heart fails to function properly. Diseased heart valves may be categorized as either stenotic, wherein the valve does not open sufficiently to allow adequate forward flow of blood through the valve, and/or incompetent, wherein the valve does not close completely, causing excessive backward flow of blood through the valve when the valve is closed. Valve disease can be severely debilitating and even fatal if left untreated, particularly if the diseased valve is the mitral valve (between the left atrium and left ventricle) or the aortic valve (between the left ventricle and the aorta). According to recent estimates, more than 80,000 patients are diagnosed with aortic or mitral valve disease in U.S. hospitals each year.

Various surgical techniques may be used to repair a diseased or damaged valve. In a valve replacement operation, the damaged leaflets are excised and the annulus sculpted to receive a replacement valve. Another less drastic method for treating defective valves is through repair or reconstruction, which is typically used on minimally calcified valves. One repair technique which has been shown to be effective in treating incompetence, particularly of the mitral and tricuspid valves, is annuloplasty, in which the effective size of the valve annulus is contracted by attaching a prosthetic annuloplasty repair segment or ring to an interior wall of the heart around the valve annulus. The annuloplasty ring is designed to support the functional changes that occur during the cardiac cycle: maintaining coaptation and valve integrity in systole while permitting good hemodynamics in diastole. Where contracting or stabilizing the valve annulus might be desirable, annuloplasty rings may also be utilized in combination with other repair techniques such as quadrangular resection, commissurotomy, shortening mitral or tricuspid valve chordae tendonae, reattachment of severed mitral or tricuspid valve chordae tendonae or papillary muscle tissue, and decalcification of the valve leaflets or annulus. The annuloplasty ring typically comprises an inner substrate of a metal such as stainless or titanium, or a flexible material such as silicone rubber or Dacron cordage, covered with a biocompatible fabric or cloth to allow the ring to be sutured to the heart tissue. Annuloplasty rings may be stiff or flexible, may be split or continuous, and may have a variety of shapes, including circular, D-shaped, C-shaped, or kidney-shaped. Examples are seen in U.S. Pat. Nos. 4,917,698, 5,061,277, 5,290,300, 5,350,420, 5,104,407, 5,064,431, 5,201,880, and 5,041,130, which are incorporated herein by reference.

Using current techniques, most valve repair procedures require a gross thoracotomy, usually in the form of a median sternotomy, to gain access into the patient's thoracic cavity. A saw or other cutting instrument is used to cut the sternum longitudinally, allowing two opposing halves of the anterior or ventral portion of the rib cage to be spread apart. A large opening into the thoracic cavity is thus created, through which the surgical team may directly visualize and operate upon the heart and other thoracic contents. Alternatively, a thoracotomy may be performed on a lateral side of the chest, wherein a large incision is made generally parallel to the ribs, and the ribs are spread apart and/or removed in the region of the incision to create a large enough opening to facilitate the surgery. Using such open-chest techniques, the large opening provided by a median sternotomy or right thoracotomy enables the surgeon to see the affected valve directly, and to position his or her hands within the thoracic cavity in close proximity to the exterior of the heart for cannulation of the aorta and/or coronary arteries to induce cardioplegia, manipulation of surgical instruments, removal of excised tissue, and introduction of an annuloplasty ring or a replacement valve through the atriotomy for attachment within the heart. However, these invasive, open-chest procedures produce a high degree of trauma, a significant risk of complications, an extended hospital stay, and a painful recovery period for the patient. Moreover, while heart valve surgery produces beneficial results for many patients, numerous others who might benefit from such surgery are unable or unwilling to undergo the trauma and risks of current techniques.

Naturally, surgical patients desire operations be performed with the least amount of intrusion into the body. Recently, a great amount of research has been done to reduce the trauma and risk associated with conventional open heart valve replacement surgery. In particular, the field of minimally invasive surgery (MIS) has exploded since the early to mid-1990s, with devices now being proposed to enable valve replacements without opening the chest cavity. Such proposed MIS heart valve repair or replacement surgeries still requires bypass, but the procedures are accomplished via elongated tubes or cannulas introduced through one or more small access incisions in the thorax, with the help of endoscopes and other such visualization techniques. Such minimally invasive procedures usually provide speedier recovery for the patient with less pain and bodily trauma, thereby reducing the medical costs and the overall disruption to the life of the patient. A minimally invasive approach also usually results in a smaller incision and, therefore, less scarring, which is an aesthetic advantage attractive to most patients. The use of a minimally invasive approach, however, introduces new complexities to surgery thus placing a greater burden on the operating surgeon. Most notably, minimally invasive approaches drastically reduce the size of the surgical field available to the surgeon for the manipulation of tissue and for the introduction of necessary surgical instruments, such as cutting devices, clamps, prosthetic holders, and so on. These complexities are especially acute in connection with heart surgery. Unlike common heart surgeries performed using a full medial sternotomy, minimally invasive heart surgery offers a surgical field that may be only as large as a resected intercostal space or a transversely cut and retracted sternum. Consequently, the introduction of tools, such as prosthetic sizing elements, valve holders, annuloplasty ring holders, and other such devices, becomes a great deal more complicated.

The majority of instruments currently available to surgeons for performing minimally invasive surgeries are devices designed for use in far less restrictive surgical fields. That is, the existing instruments have characteristics which are not conducive for use in restrictive surgical fields. For example, in heart surgery, the majority of implements available to hold or retain various heart devices or tools (e.g., heart valves and annuloplasty rings) in a minimally invasive procedure either are too short to enable easy introduction of prostheses to the target site and/or have shafts which lack the necessary malleability or flexibility to enable proper orientation of the prostheses at the distal end of the shaft. Examples of such prior art devices are disclosed in U.S. Pat. No. 4,679,556 to Lubock et al.; U.S. Pat. No. 5,531,785 to Love et al.; U.S. Pat. No. 5,360,014 to Sauter et al.; U.S. Pat. No. 5,403,305 to Sauter et al.; U.S. Pat. No. 5,476,510 to Eberhardt et al.; U.S. Pat. No. 5,489,296 to Love et al.; and U.S. Pat. No. 5,560,487 to Star.

One technique proposed for minimally invasive annuloplasty repair, disclosed in U.S. Pat. No. 5,972,030, involves a delivery handle that enables the annuloplasty ring carried thereon to pivot 90°. That is, the ring mounted on a rigid template is aligned along the handle axis during insertion through an access port, and is then rotated from the proximal end of the handle to a perpendicular implantation orientation. This technique relies on an oval-shaped access port to pass the ring and template into the chest cavity, and thus additional special implements are required.

What is needed, therefore, are devices and methods for carrying out heart valve repair that reduce the trauma, risks, recovery time and pain that accompany current techniques. The devices and methods should facilitate surgical intervention without the need for a gross thoracotomy. In particular, the devices and methods should allow for the introduction of surgical instruments to facilitate heart valve repair. The devices and methods should enable the implantation of annuloplasty repair segments or rings of various shape, size, and stiffness without the need for excessive additional implements.

SUMMARY OF THE INVENTION

The present invention provides a holder for an annuloplasty repair segment, comprising an elongate template adapted to attach to the repair segment. The template is adapted to pass in a generally linear shape through a tube, and is convertible from the generally linear shape to a curved shape. In one embodiment, the template is flexible, and may be biased toward the curved shape. The curved shape may be two- or three-dimensional. A deflection mechanism may be provided for actively converting the template between the linear shape and the curved shape. In one embodiment, the holder further includes an anchor mandrel to which the template is releasably attached, and a tether maintaining a connection between the template and the anchor mandrel when released.

In a further embodiment, a combined annuloplasty repair segment and holder is provided, where the holder has a template with a generally linear shape in at least one position and is adapted to undergo a shape change along its length. The repair segment attaches to the template and is configured to assume the changed shape of template. The template may be capable of a temperature-induced shape change between the linear shape and changed shape. In one embodiment, template is flexible, but unbiased from the linear shape, and a holder further includes a biasing member adapted to insert within the template so as to bias the template toward the curved shape. A handle may be attached to the template for manipulating the template to position the repair segment into proximity with a valve annulus. The template may be provided with suture location markers to facilitate suture alignment with anatomical landmarks.

In a further embodiment, an annuloplasty repair segment delivery system of the present invention includes a delivery sheath, an anchor mandrel, and an elongate template. The anchor mandrel is slidably disposed within the sheath near a distal end thereof, yet is restrained from exiting the sheath. The template is adapted to attach to a flexible annuloplasty repair segment and is releasably attached to the anchor mandrel. The template is convertible from a generally linear shape within the sheath, to a curved shape when ejected from the distal end of the sheath. The system further may include a tether connecting the template and anchor mandrel when released. In one embodiment, the template is biased toward the changed shape, which may be a two- three-dimensional curve. The template may include a handle portion and a forming portion, the forming portion being biased into a curved shape and being attached to the repair segment so that the segment assumes the curved shape. In one embodiment, the forming portion inserts within the segment.

In still another aspect of the present invention, a method of implanting an annuloplasty repair segment in a heart valve annulus comprises the steps of:

1. providing a holder having a flexible template adapted to attach to an annuloplasty repair segment, the template being convertible from a generally linear shape to a curved shape;
2. attaching an annuloplasty repair segment to the flexible template;
3. delivering the repair segment attached to the template to a heart valve annulus;
4. causing the template and repair segment to simultaneously undergo a shape change; and
5. attaching the annuloplasty repair segment to the annulus.

The method may also include a step of delivering the annuloplasty repair segment attached to the template through a minimally-invasive tube. The minimally invasive tube may be inserted through an access incision in the chest wall, or through an access incision in the peripheral vasculature and through vascular system, both into proximity within the annulus. The method may include releasing the template from the end of the tube, and maintaining a tether connection between the template and an anchor mandrel from within the tube.

A further understanding of the nature and advantages of the invention will become apparent by reference to the remaining portions of the specification and drawings.

BRIEF DESCRIPTION OF THE DRAWINGS

FIG. 1 is an elevational view of a holder of the present invention having an annuloplasty repair segment attached to a flexible distal template;

FIG. 2 is an elevational view of an alternative holder of the present invention having an annuloplasty repair segment attached to a flexible distal template;

FIG. 4 is an elevational view of a still further holder of the present invention having an annuloplasty repair segment attached to a distal template having markers;

FIG. 5 is an elevational view of another holder of the present invention having an annuloplasty repair segment attached to a flexible distal template that can pivot with respect to a proximal handle;

FIGS. 6A and 6B are elevational views of the deployment of the holder of FIG. 5;

FIGS. 7A and 7B are elevational views of another holder of the present invention having an annuloplasty repair segment attached to a distal multi-segmented template that can curl with respect to a proximal handle upon actuation of a pull string;

FIGS. 8A–8C are perspective views of a further holder of the present invention having an annuloplasty repair segment attached to a distal template that is biased to curl in three-dimensions with respect to a proximal handle;

FIGS. 9A and 9B are perspective views of an annuloplasty delivery system of the present invention having an annuloplasty repair segment attached to a template that is biased to curl when ejected from a proximal delivery tube;

FIG. 10 is a perspective exploded view of the annuloplasty delivery system of FIGS. 9A and 9B;

FIG. 11 is an enlarged perspective view of the distal end of the annuloplasty delivery system of FIGS. 9A and 9B;

DESCRIPTION OF THE PREFERRED EMBODIMENTS

Figure 3A:
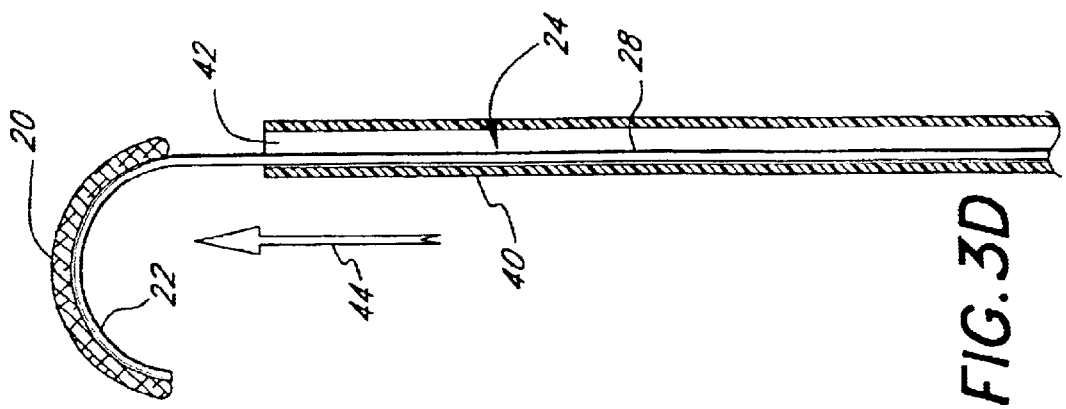
FIGS. 3A–D are elevational views of the deployment of the holder of FIG. 1 from within a delivery tube.

The present invention provides a number of different templates for delivering and facilitating implantation of annuloplasty rings or repair segments. It should be understood that the term annuloplasty ring or repair segments refers to any generally elongated structure used in annulus repair, whether straight or curved. For example, an annuloplasty ring is conventionally understood to provide either a complete or substantially complete loop sized to correct a misshapen and or dilated native annulus. In many instances, a partial ring or even a straight repair segment may be used around just a template of the annulus, such as around the posterior edge. Consequently, the term "annuloplasty repair segment" as used herein is intended to encompass all of such structures. Additionally, although annuloplasty repair devices are typically suture-permeable, the use of the invention to implant other structures which are attached to the annulus without passage of sutures therethrough is also contemplated.

A first embodiment of the present invention is illustrated in FIG. 1 in which an annuloplasty repair segment 20 is attached to a curved template 22 of a delivery holder 24. The annuloplasty repair segment 20 is flexible and conforms to the curved template 22 by virtue of a plurality of attaching sutures 26, or other similar expedient.

The holder 24 comprises the curved template 22 defining a distal end, and a generally straight, elongated shaft template 28 defining a proximal end. Depending on the implantation technique, the shaft 28 may be flexible or rigid. The curved template 22, on the other hand, is highly flexible, preferably elastic. Specifically, curved template 22 may be formed of a biocompatible metal such as stainless-steel or Elgiloy, or from a super-elastic material such as Nitinol. The material used for the curved template 22 may be the same as that used for the shaft portion 28, or the two portions may be formed of different material and connected using conventional means. The usage of the holder 24 will be described below with respect to FIGS. 3A–3C.

FIG. 2 illustrates an alternative embodiment of the present invention similar to that shown in FIG. 1, with an annuloplasty repair segment 20 supported on a curved wire-like template 30 of a holder 32. Again, the holder 32 comprises the wire-like template 30 on the distal end, and a shaft potion 34 on the proximal end.

In contrast to the suture attachment means shown in FIG. 1, the curved wire-like template 30 passes through the body of the annuloplasty repair segment 20 to secure it thereto. In this regard, therefore, the annuloplasty repair segment 20 must be sufficiently permeable for the wire-like template 30 to pass therethrough. In one embodiment, the annuloplasty repair segment 20 comprises an elastic inner core (not shown) surrounded by a tubular fabric covering 36. The wire-like template 30 may therefore be passed between the inner core and the fabric covering 36, or may even be embedded within the inner core for a more secure coupling. The inner core may take a number of forms, including a solid metal rod such as titanium, a metal rod in combination with a silicone sleeve, or a silicone rod. Various other annuloplasty repair segment constructions are well-known in the art, and are incorporated herein.

Figure 3B:
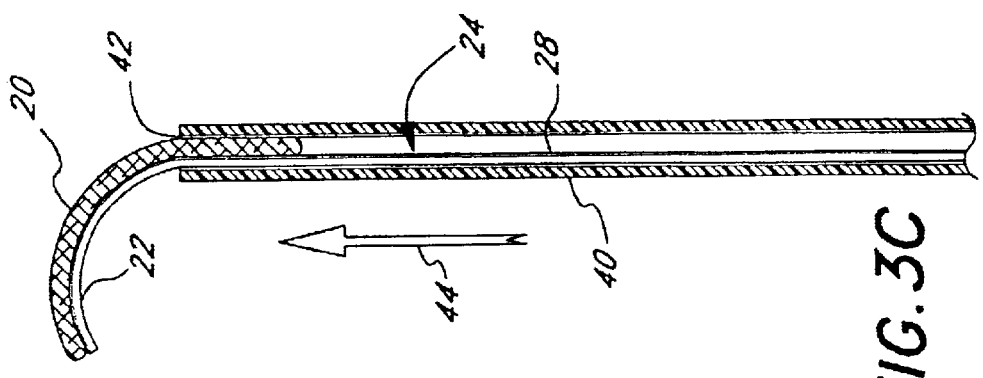
Figure 3C:
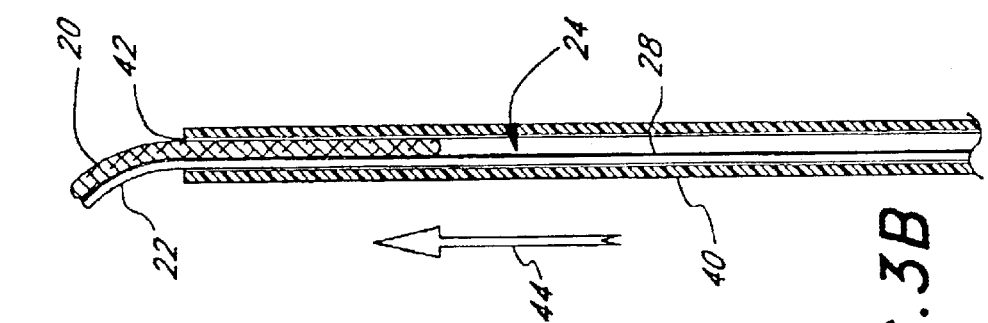

FIGS. 3A–3C illustrate a series of positions of the combined annuloplasty repair segment 20 and holder 24 of FIG. 1 being delivered through a delivery tube 40, such as a cannula or catheter. It should be understood that the same operation applies to the combined ring 20 and holder 34 shown in FIG. 2.

The delivery tube 40 comprises a proximal end (not shown) and an open distal end 42. In use, the combined annuloplasty repair segment 20 and holder 24 are located as shown adjacent the distal end 42, or are advanced into that positioned through the tube 40. It should be noted that the curved template 22 on the distal end of the holder 24 (and the attached ring 20) assumes a straightened or elongate configuration when located within the tube 40.

Figure 3D:
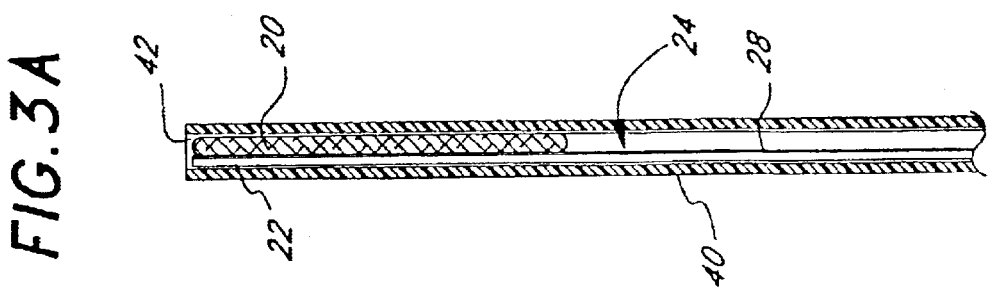

As will be explained in greater detail below, the distal end 42 is advanced into proximity with the site at which the annuloplasty repair segment 20 will be implanted; namely, a distended or otherwise damaged heart valve annulus. Subsequently, as seen FIGS. 3B–3D, the combined annuloplasty repair segment 20 and holder 24 are advanced from the distal end 42 in the direction of arrow 44. By virtue of the elasticity of the curved template 22, the annuloplasty repair segment 20 ultimately undergoes a shape change to the curved shape as seen in FIG. 3D. As the curved template 22 passes from the distal end 42 of the tube 40, its own spring-bias causes it to revert to its original shape. It should be noted that the spring bias might be in more than one plane. That is, the resulting curved configuration may be a three-dimensional shape as desired.

The holder 24 may be advanced from the open mouth 42 by either distal displacement of the holder 24 with respect to the fixed tube 40, or by proximal displacement of the tube 40 with respect to the fixed holder 24. That is, the holder 24 can be pushed from within the tube 40, or the tube can be retracted to expose the ring 20 and curved template 22. In an exemplary embodiment, the shaft 28 extends a sufficient distance in the proximal direction to emerge from within the proximal end (not shown) of the tube 40, and is manipulated by a handle, or other such means.

FIG. 4 illustrates an alternative embodiment of the present invention in which an annuloplasty repair segment 50 is removably attached to an elongate, preferably straight holder 52. In this embodiment, the combined ring 50 and holder 52 are sized to be advanced into implantation position through a minimally invasive access tube or catheter, with a distal template of the holder 52 remaining straight so that the annuloplasty repair segment 50 also remains straight. The straight ring 50 may be attached to a short section of annulus that has been plicated or otherwise tightened where the need to repair the entire annulus is absent. In this regard, the holder 52 need not be flexible, the advantage being the reduced profile or cross-sectional size of the holder and repair segment combination that enables minimally-invasive passage through a tube such as a cannula or catheter. In a preferred embodiment, the maximum cross-sectional dimension of the holder and repair segment combination is sufficiently small, for example 5–10 mm, so as to pass through known minimally invasive cannulas or catheters.

Alternatively, the material of the holder 52 may be such that it changes shape and forms a curve upon reaching body temperature. That is, certain shape memory metals (e.g., Nitinol) may be used that undergo a shape change upon crystalline transformation between two temperatures.

A plurality of markers 54 are also provided on the distal portion of the holder 52 to indicate suture placement. Such markers 54 may be, for example, colored or contrasting lines or dots, or may be radiopaque or otherwise highly visible, such as fluorescent. Location and spacing of the individual markers 54 may correspond to particular anatomical landmarks, as previously measured using an endoscope, for example.

FIG. 5 illustrates a still further embodiment of the present invention in which an annuloplasty repair segment 60 is fastened to a flexible template 62 connected to the distal end of the insertion handle 64 at a hinge 66. The ring 60 attaches to the flexible template 62 using one or more mounting sutures 68. The mounting suture(s) 68 desirably pass through the suture-permeable ring 60, or may be looped therearound, and are threaded through apertures or guides provided in the template 62 and secure thereto, such as with knots. A plurality of cutting guides or prompts 70 are also provided at spaced intervals on the flexible template 62 across which the mounting sutures 68 extend. The cutting prompts 70 may take the form of a pair of raised notches across which a suture 68 extends such that a scalpel blade may be inserted between the notches to sever the suture. Examples of such cutting prompts 70 are seen in U.S. Pat. No. 5,683,402, hereby expressly incorporated by reference.

FIGS. 6A and 6B schematically illustrate several steps in implantation of the annuloplasty repair segment 60 and operation of the template 62. The assembly of the ring 60, template 62, and handle 64 is first inserted through an access incision 72 in the wall of the chest (schematically shown at 74). After locating the annuloplasty repair segment 60 in proximity with the damaged annulus, the flexible template 62 pivots with respect to the handle 64 at the hinge 66. Such pivoting may be accomplished using a push or pull mechanism, such as a suture 76 connected at the extreme distal most tip of the template 62 and passing through a series of guides or pulleys (not shown) within the handle 64. In a preferred embodiment, the hinge 66 permits the flexible template 62 to pivot an angle of less than 90° with respect to the handle 64, after which point further pulling on the suture 76 causes the template 62 to bend, as seen in FIG. 6B. For example, hinge 66 may permit the template 62 to pivot an angle of between about 70–85°, more preferably about 80°. In this manner, stress imposed on a flexible template 62 is reduced in contrast to simply bending the template through the entire angular rotation.

FIGS. 7A–7C illustrate a still further embodiment of present invention in which an annuloplasty repair segment 80 is secured to a multi-segmented template 82 provided on the distal end of a handle 84. The template 82 comprises a series of segments 86 linked together at pivot points 88. By forming the segments 86 with cutouts 90, for example, the segmented template 82 can form the curvature seen FIGS. 7B, but is structurally prevented from curling in the opposite direction.

An exemplary cross-section of a segment 86 is seen in FIG. 7C and comprises a generally rectilinear shape having a groove or depression 92 on one end for receiving the annuloplasty repair segment 80, and a through bore 94. The through bores 94 in each of the segments 86 are aligned to receive a pre-biased bend wire 96. FIG. 7A is an exploded view, while FIG. 7B shows the components assembled with the bend wire 96 causing the segmented template 82 to form the aforementioned curvilinear shape. In addition, the annuloplasty repair segment 80 conforms to the shape of the bend wire 96 and template 82.

In use, the assembled components, including the bend wire 96, may be advanced through a minimally invasive introducer tube, such as a cannula or a catheter. Depending on the rigidity of the introducer tube, the assembly seen in FIG. 7B may be partially or completely straight. Further advancement of the assembly from the open distal end of the introducer tube permits the bend wire 96 to curl the template 82 and annuloplasty repair segment 80 into the configuration shown. This technique is much like that shown in FIGS. 3A–3C for the first two embodiment illustrated.

Alternatively, the assembly minus the bend wire 96 may be advanced into proximity with the damaged annulus through an access incision, or through a minimally invasive introducer tube. Subsequently, and after projection of the annuloplasty repair segment 80 from the introducer tube, if used, the bend wire 96 may be introduced into the proximal end of the handle 84, as indicated by the arrow 98 in FIG. 7B. As the bend wire 96 advances through the aligned through bores 94, the resulting curvilinear shape as seen in FIG. 7B is attained.

FIGS. 8A–8C illustrate a further holder 100 of the present invention having an annuloplasty repair segment 102 attached to a distal template 104 that is biased to curl in three-dimensions with respect to a proximal handle 106. The annuloplasty repair segment 102 may be attached to one side of the template 104, as in the earlier embodiments, or the template may be sized to insert within the repair segment. In the latter instance, the template 102 may be a wire that fits within a receiving bore of the annuloplasty repair segment 102, or the wire may simply slide between an outer fabric cover and inner structure of the repair segment 102.

In use, the holder 100 may be disposed within and ejected from a delivery tube, such as with the earlier embodiment seen in FIGS. 3A–3B. Once the distal end of the holder 100 emerges from within the tube, the pre-biased template 104 assumes its particular three-dimensional shape, and so does the attached annuloplasty repair segment 102. Ideally, the shape of the template 104 re-orients the annuloplasty repair segment 102 from being aligned with the tube axis, to defining a ring or ring segment that lies in a plane angled with respect to the tube axis. As best seen in FIG. 8A, the ring or ring segment desirably lies in a plane that is nearly perpendicular to the tube axis, which is typical as the native valve annulus lies at a similar orientation with respect to the direction of insertion of the delivery tube. The surgeon then attaches the segment 102 in a manner to correct the affected valve annulus, and disconnects the template 104. If the template 104 is attached via sutures, it is disconnected with a scalpel. If the template 104 is inserted within the body of the segment 102, the surgeon braces the segment with forceps, or otherwise, and retracts the template from within. The template may be made of a suitable metal or polymer. A lubricious polymer, such as silicon, may be desirable if the template inserts within the segment 102 to facilitate removal therefrom.

FIGS. 9A–9B, 10 and 11 illustrate an annuloplasty delivery system 120 of the present invention having an annuloplasty repair segment 122 attached to a template 124 that is biased to curl when ejected from a proximal delivery sheath 126. The template 124 includes a proximal handle section 128 and a distal forming section 130. The forming section attaches to or inserts within the annuloplasty repair segment 122, and causes the segment to assume the same shape. The handle section 128 is enlarged relative to the forming section 130 and includes a plurality of through holes 132 to which a tether 134 attaches. The tether 134, in turn, initially coils around and attaches to a post 136 provided on an anchor mandrel 138. The anchor mandrel 138 is sized to fit and slide within a delivery tube 140 concentrically disposed within the delivery sheath 126. The anchor mandrel 138 further includes a rectangular pin 142 on its distal end that mates with a similarly-sized cavity 144 in the proximal end of the handle section 128 of the template 124.

In use, the template 124 mates with the anchor mandrel 138, and the two as well as the annuloplasty repair segment 122 are housed within the delivery tube 140. The delivery tube 140 is initially retracted within the delivery sheath 126 that is typically rigid and inserted though a chest incision or so-called stab wound. As before, however, the delivery sheath 126 may take the form of an elongated, flexible catheter for percutaneous, vascular insertion.

After the distal end of the delivery sheath 126 is positioned near the valve annulus site, the delivery tube 140 is advanced from within the delivery sheath, as seen in FIGS. 9A and 9B. Using a pusher rod (not shown), the anchor mandrel 138 is at least partially advanced out of the end of the delivery tube 140. The anchor mandrel 138 may include an enlarged cylindrical proximal end that is stopped at the end of the delivery tube 140 by a flange or tab. At least the post 136 extends from the tube 140, as shown. The rectangular pin 142 and cavity 144 may engage with an interference fit, or a more positive coupling may be provided. In either case, the surgeon disengages the two elements to release the template 124. The tether 134 maintains a connection between the anchor mandrel 138 and template 124, and thus between the sheath 126 and template.

By manipulating the handle template 128, the surgeon can maneuver the curled annuloplasty repair segment 122 into the proper position, and attach it to correct the affected annulus. At this stage, the template 124 may be detached from the annuloplasty repair segment 122 by severing connecting sutures, if the template is attached to the side of the segment. Alternatively, if the forming portion 130 inserts within the repair segment 122, it may be retracted by bracing the segment and pulling the template 124 free, such as by pulling the tether 134.

The advantage of such a system as shown in FIGS. 9–11 is the ability of the surgeon to freely maneuver the annuloplasty repair segment 122 into position, within the constraint of an attached handle. Moreover, the template 124 maintains the proper repair segment shape while the attachment procedure is done. The annuloplasty repair segment 122 is typically relatively flexible, and the reinforcement of the forming portion 130 greatly reduces the surgeon's task, especially in the small spaces of minimally-invasive surgeries. Finally, although a semi-circular, planar shape of the forming portion 130 is shown, other shapes such as a three-dimensional shape may be utilized, or the shape may be customized based on patient need.

Methods of Use

FIGS. 12–22 illustrate two exemplary minimally invasive techniques for repairing a heart valve annulus using the present invention. FIGS. 13–16 pertain to an aortic valve repair, while FIGS. 17–22 pertain to a mitral valve repair. These procedures involve creation of an access channel from the outside of the body through the patient's chest cavity, with the heart being stopped and the patient put on bypass. The repair is done with the affected heart valve being exposed through the channel. Other procedures are contemplated, however, including a wholly vascular approach with elongated, flexible catheters inserted through the femoral artery, for example, eliminating the chest incision. Therefore, the following methods should be considered exemplary only, and illustrative of the ultimate delivery and implantation of the annuloplasty devices described herein.

Aortic Procedure

Figure 12:
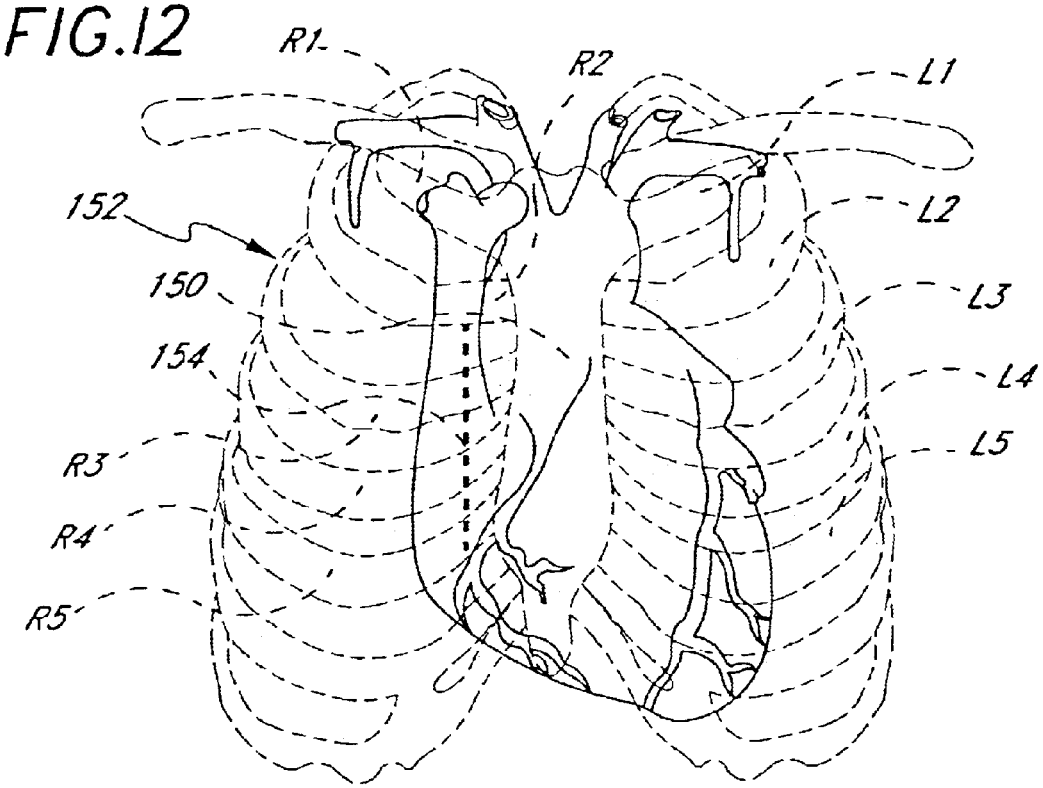
FIGS. 12 and 12A are schematic illustrations depicting a human chest and the disposition of a right parasternal incision in connection with an aortic surgery procedure in accordance with the present invention.

Referring now to FIG. 12, in a typical human, a sternum 150, a planary bone structure centrally disposed in the chest, is connected to a plurality of ribs 152 by respective costal cartilages R1, R2, R3, R4, R5, and L1, L2, L3, L4, L5. The heart and great vessels are located within a tissue sack (pericardium), located beneath the sternum, extending laterally under the costal cartilages and ribs, with the aorta disposed in part underlying the second and third right costal cartilages R2 and R3 and a portion of the right coronary artery located generally underlying the vicinity of the fourth and fifth right costal cartilages R4 and R5.

In accordance with one aspect of the present invention, it has been determined that a surgery on portions of the heart and great vessels located between a point approximately three centimeters above supra annular ridge and the mid-ventricular cavity, can be effected with minimal invasion, without a median sternotomy, or other gross thoracotomy, by, as illustrated in FIG. 12, making a relatively short parasternal incision 154 extending across a predetermined number of costal cartilage, e.g., a right parasternal incision extending from the lower edge of the second costal cartilage R2 to the superior edge of the fifth costal cartilage R5 and removing one or more costal cartilages, e.g., the third and fourth costal cartilages, R3 and R4. It has been determined that over a period of time the chest wall in the area of the resected cartilages becomes stable secondary to scarring of the remaining tissue. In effect, scar tissue resulting from the procedure functionally replaces the excised cartilage, providing a relatively rigid chest wall.

This procedure can be readily employed to perform operations on structures located on portions of the heart and great vessels located between a point approximately three centimeters above supra annular ridge and the mid-ventricular cavity. As will be more fully described, the procedure is of particular utility with respect to surgery to repair or replace the aortic valve. Specifically, in the context of exemplary surgery to replace an aortic valve, the patient is anesthetized and intubated, and placed supine on the operating room table. Preferably, defibrillator pads are placed on the patient's back and anterior left chest, and a transesophageal echocardiography probe is placed to access the etiology of the aortic valve disease and to assist in removing air from the heart after completion of the operation.

Figure 12A:
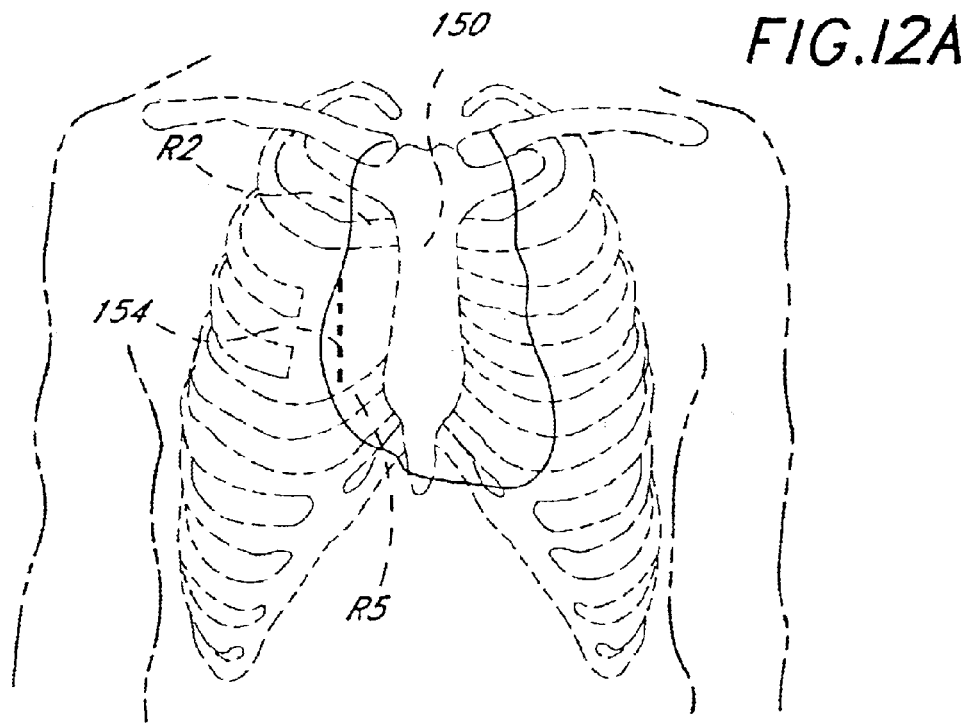
Figure 13:
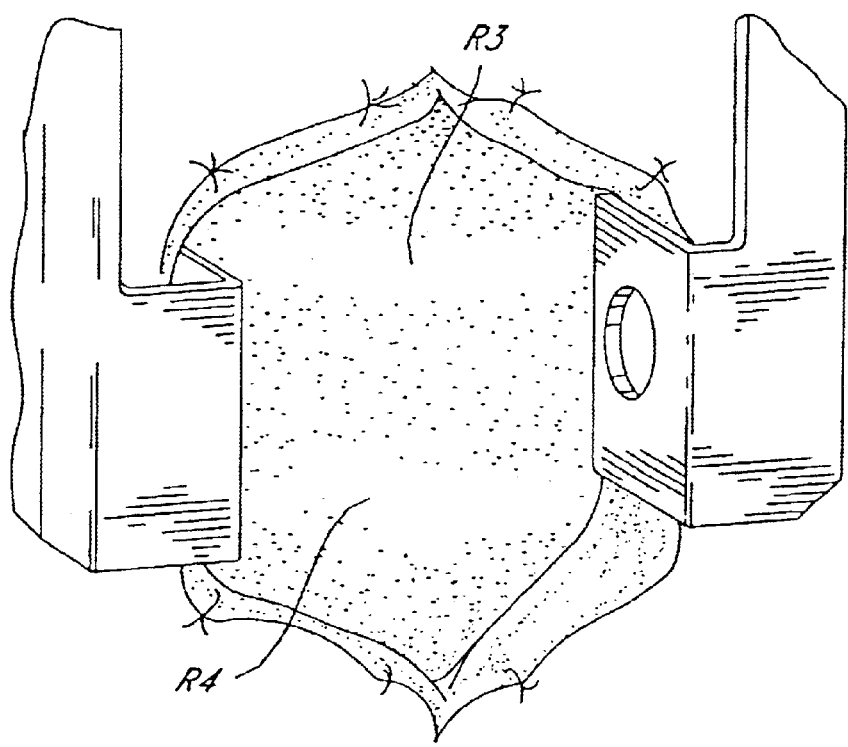
FIG. 13 is a pictorial illustration depicting the right parasternal incision of FIG. 12 showing respective costal cartilages.
Figure 14:
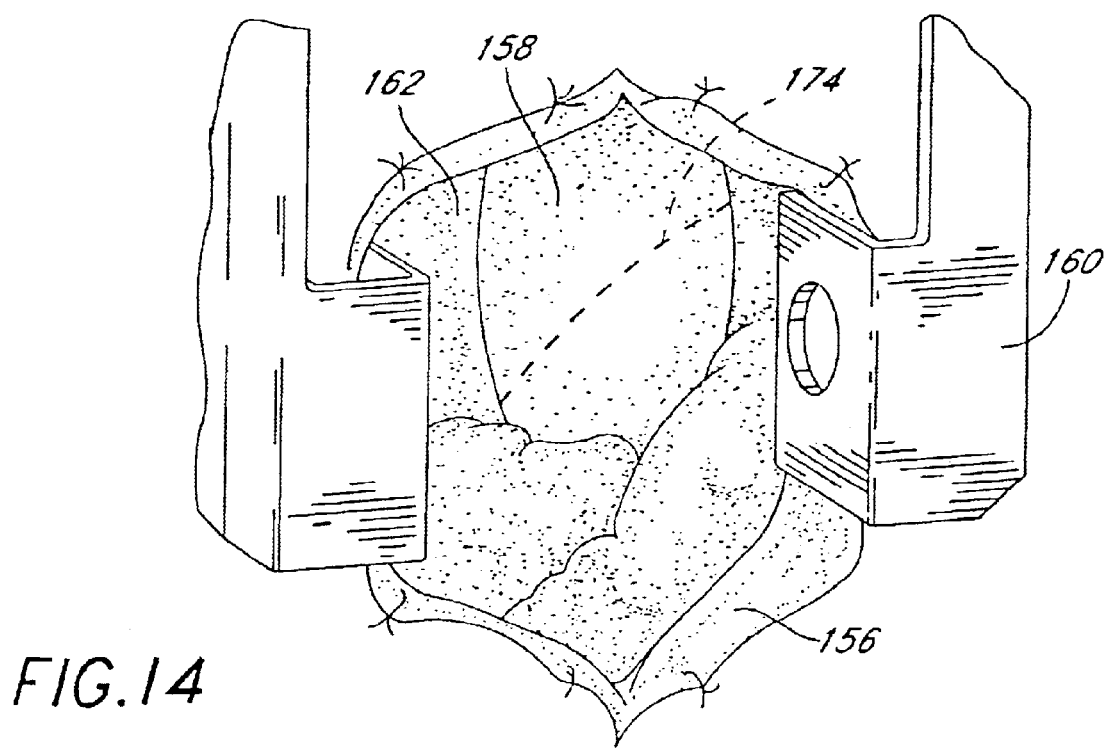
FIG. 14 is a pictorial illustration depicting the right parasternal incision of FIG. 12 after respective costal cartilage units are excised and incision retracted.

Referring to FIGS. 12 and 12A, a right parasternal incision is made extending from the lower edge of the second costal cartilage R2 to the superior edge of the fifth costal cartilage. The pectoral major muscle is divided, exposing the second, third, and fourth intercostal spaces, and the third and fourth costal cartilages R3 and R4 as shown in FIG. 13. The third and fourth costal cartilages R3 and R4 are totally excised (FIG. 12). The right internal thoracic artery is ligated just below the second costal cartilage R2 and just above the fifth costal cartilage R5. Intercostal muscles and pleura are incised lateral to the edge of the sternum, entering the right pleural cavity. As shown in FIG. 14, the pericardium 156 is then incised, exposing the ascending aorta 158, and is stitched back. The incision is held open using a conventional chest retractor 160.

A cardiopulmonary by-pass is then established. Typically, a common femoral artery and vein are exposed and, after infusion of an anti-coagulant, e.g., heparinization, are cannulated. Catheters are placed in the femoral artery and in femoral vein, respectively. Adequate venous drainage maybe obtained by utilizing a long venous cannula disposed so that the tip of the cannula passes through the right atrium and preferably into the superior vena cava 162 (FIG. 14). Alternatively, venous return can be affected by introducing an appropriate catheter into the right atrial appendage. Catheters direct the blood to a conventional heart-lung machine (not shown) that oxygenates the blood and pumps it back under pressure to the patient.

Figure 15:
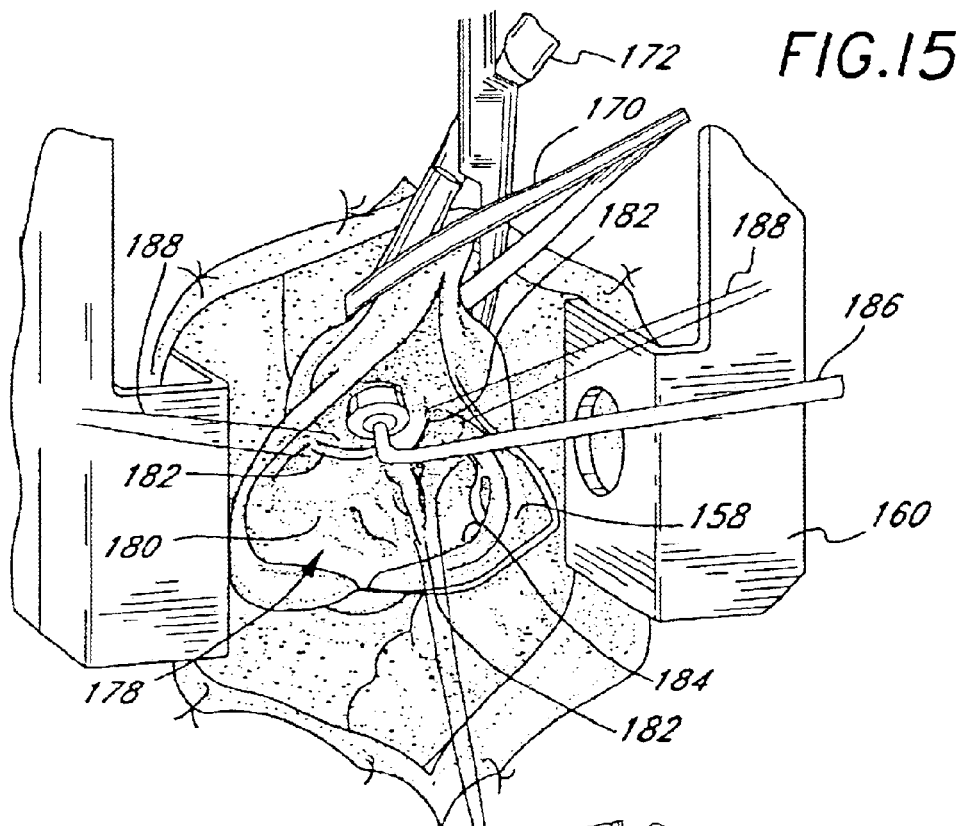
FIG. 15 is a pictorial illustration depicting the right parasternal incision of FIG. 12 after the aortic valve is removed, with traction sutures placed at the commissures.
Figure 16:
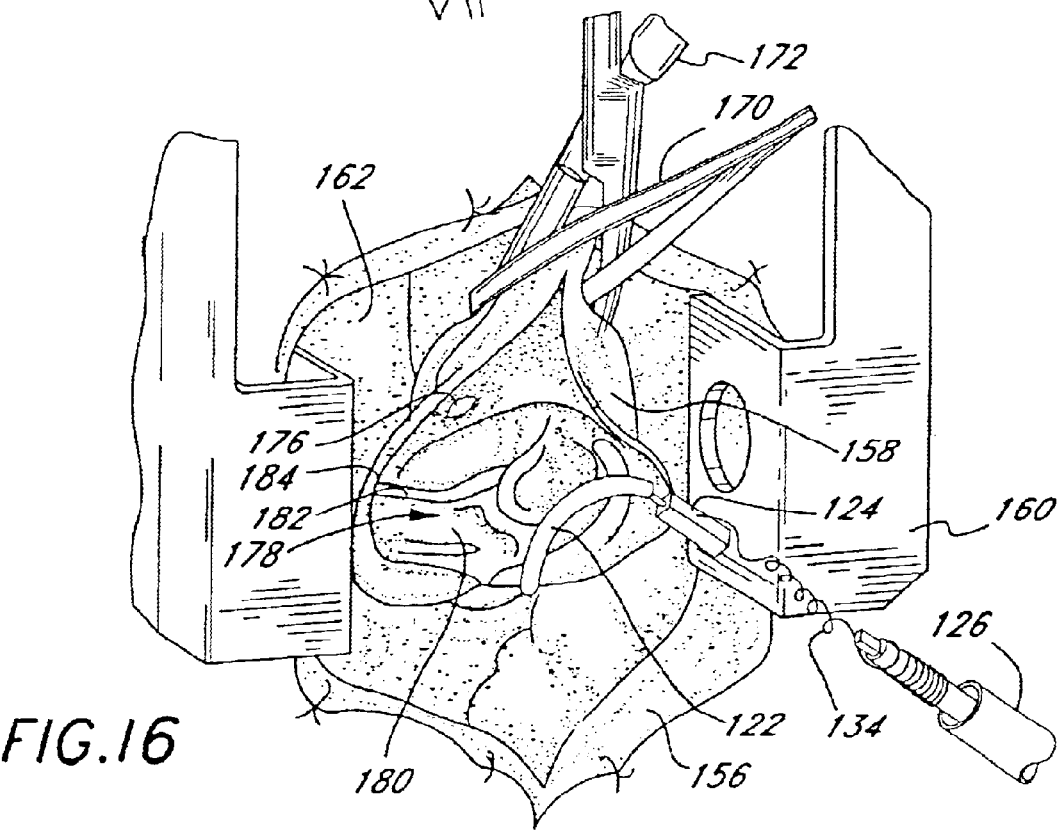
FIG. 16 is a pictorial illustration depicting the right parasternal incision of FIG. 12 after the aorta is opened to expose the aortic valve, and injection of cardioplegia into the coronary ostia.

After catheters are placed, the heart is excluded from circulation. For example, the aorta 158 is suitably encircled with umbilical tape 170 and the ascending aorta cross clamped with a right angle clamp 172. The aorta is then incised along line 174 in FIG. 14 to expose the coronary ostia 166 and the aortic valve 178, as seen in FIG. 15. Aortic valve 178 includes a plurality, typically three, of leaflets (valve cusps) 180, joined at respective commissures 182, and surrounded by a relatively fibrous aortic annulus 184. Cardiac function is arrested, by e.g., by administering cardioplegia into the ascending aorta. Typically, after performing the aortatomy, a suitable cardioplegia is introduced into the left coronary artery. Preferably, a suitable cardioplegia fluid, such as a cold potassium solution is infused through a catheter 186 inserted in coronary ostia 176. Sutures 188 are the suitably placed just above each commissure 182, and clamped under tension to a drape (not shown) surrounding the operating site. This elevates the aortic root (e.g., aortic annulus 184) into the operative field.

Aortic valve 178 is then repaired. For example, referring to FIG. 16, the annuloplasty delivery system 120 of FIGS. 9–11 is introduced into the surgical field and the annuloplasty repair segment 122 attached to the template 124 is released into proximity of the annulus 184 from the delivery sheath 126. The tether 134 maintains a connection between the template 124 and delivery sheath 126 as the repair segment 122 is maneuvered and secured into a corrective position in the annulus 184. Various implements are known for manipulating and suturing surgical devices in tight spaces, including robotically-assisted forceps and suture needles or stapling mechanisms, and will not be described or shown here. Finally, the template 124 is disengaged from the repair segment 122, and the annuloplasty delivery system 120 removed from the surgical site.

At the completion of the repair, the aortatomy is closed with sutures. Air is then removed from the heart through the aorta with the assistance of the transesophageal echocardiography probe; all air bubbles are preferably removed from the heart by removing clamp 74 to restore blood flow, and inflating the lungs, until blood flows through the closure sutures, then tightening the sutures.

Mitral Procedure

In another aspect of the present invention, a similar incision as that described above with reference to FIGS. 12 and 12A, can be used in performing surgery to repair or replace a mitral valve. More specifically, referring to FIG. 12A, a parasternal incision approximately 10 cm in length is made over the third and fourth intercostal cartilages R3 and R4. The pectoralis major muscle is then divided longitudinally, exposing the third and fourth cartilages R3, R4. The cartilages R3, R4 are completely resected and the internal thoracic artery (not shown) is then ligated and divided. The pericardium is opened and suspended under tension to the drapes of the patient.

Figure 17:
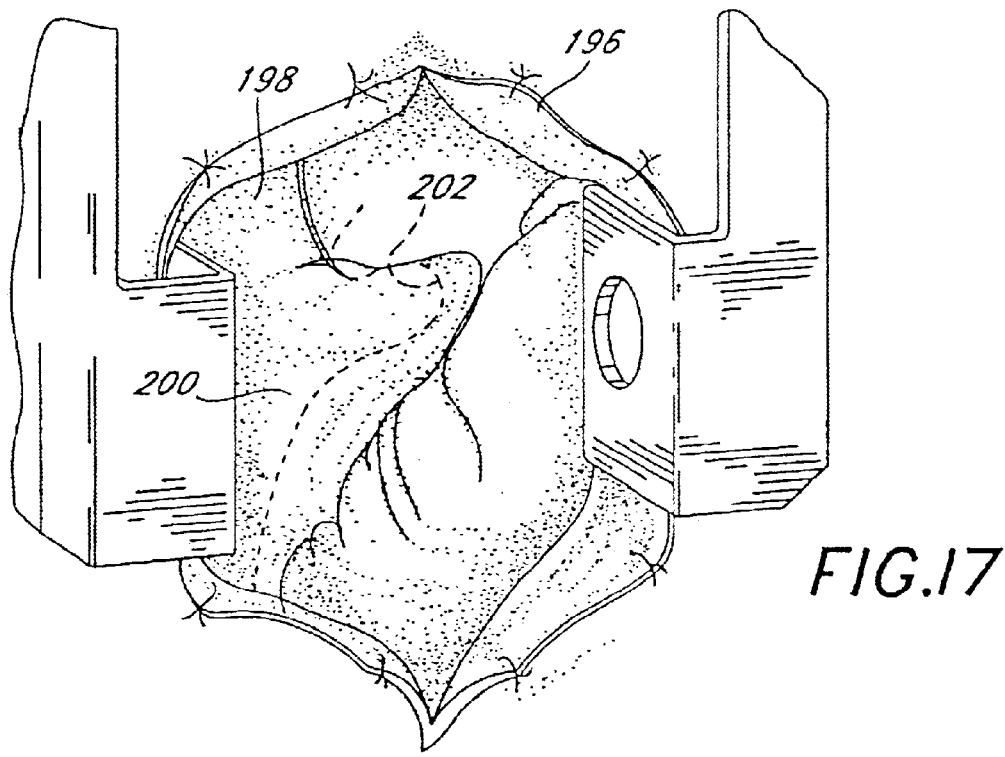
FIG. 17 is a pictorial illustration of the implantation of an annuloplasty ring of the present invention to repair the aortic valve.

Referring to FIG. 17, the resulting wound provides access into the chest cavity and particularly exposes the first portion of the ascending aorta 196, the superior vena cava 198 and the right atrium 200. The wound also provides access for making a planned incision 202 into the right atrium 200.

Figure 18:
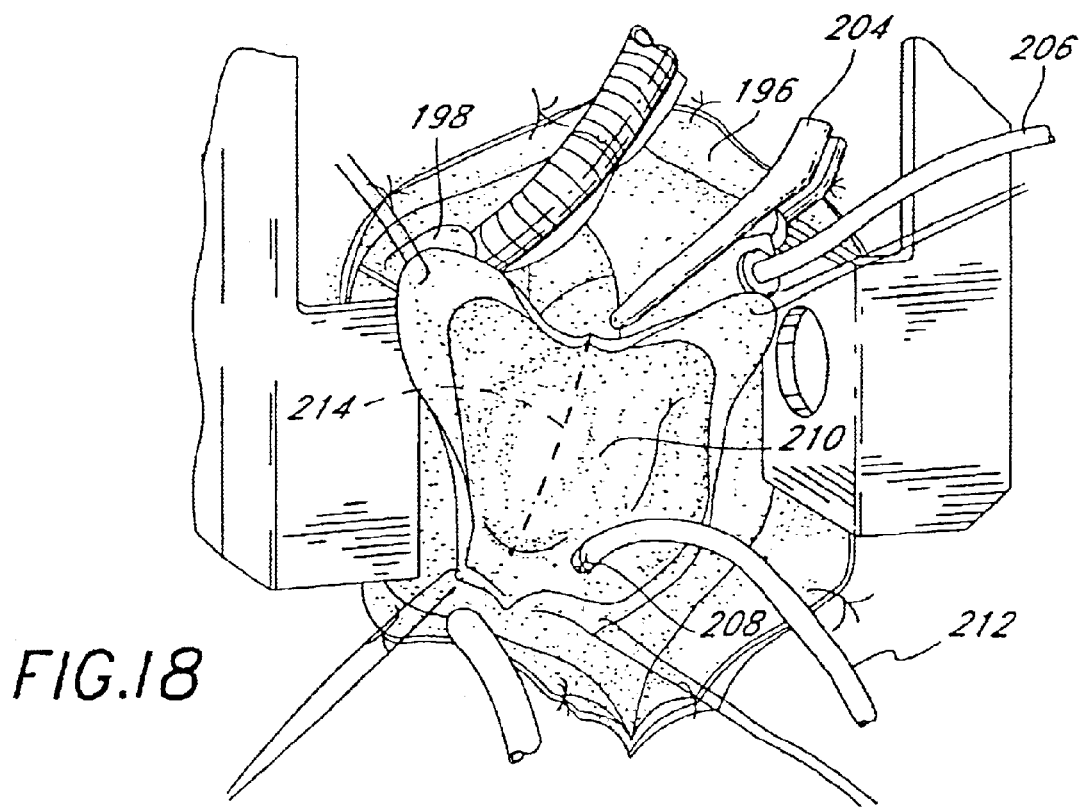
FIG. 18 is a pictorial illustration depicting the surgery field of FIG. 17 after an incision of the right atrium.

Referring to FIG. 18, prior to making the incision 202 into the right atrium 200, the patient must be cannulated so that the heart may be bypassed from blood flow during the surgery on the heart. In that connection, a first cannula (not shown) is inserted directly into the superior vena cava 198. A second cannula may be inserted into the inferior vena cava, either via the right atrium 200 or via a venous cannula introduced through a femoral vein as known in the art. Arterial return is established by a third cannula that may be inserted either directly into the ascending aorta 196 or through a femoral artery.

Once cannulation is complete, a cross clamp 204 is applied to the ascending aorta 196 as shown in FIG. 18 to occlude blood flow. Antegrade cardioplegia is then applied directly into the ascending aorta proximal of the clamp via a cardioplegia catheter 206. Bypass is established and then the heart progressively diminishes its beating activity until it ceases beating altogether. The incision 202 into the right atrium 200 is made and the tissue draped back to expose the coronary sinus 208 and intra-arterial septum 210 (FIG. 18). Additional cardioplegia is introduced, as necessary, in a retrograde fashion into the coronary sinus 208 with a retrograde cardioplegia catheter 212. The retrograde cardioplegia catheter 212 can be either a conventional retrograde catheter or an occluding balloon catheter to ensure proper introduction of the cardioplegia without leakage. The stage is then set to cut the intra-atrial septum 210 along an incision line 214 and thereby expose the dome of the left atrium. The incision 214 is made in the intra-atrial septum 210 starting at the foramen ovale and extending inferiorly and superiorly into the dome of the left atrium.

Figure 19:
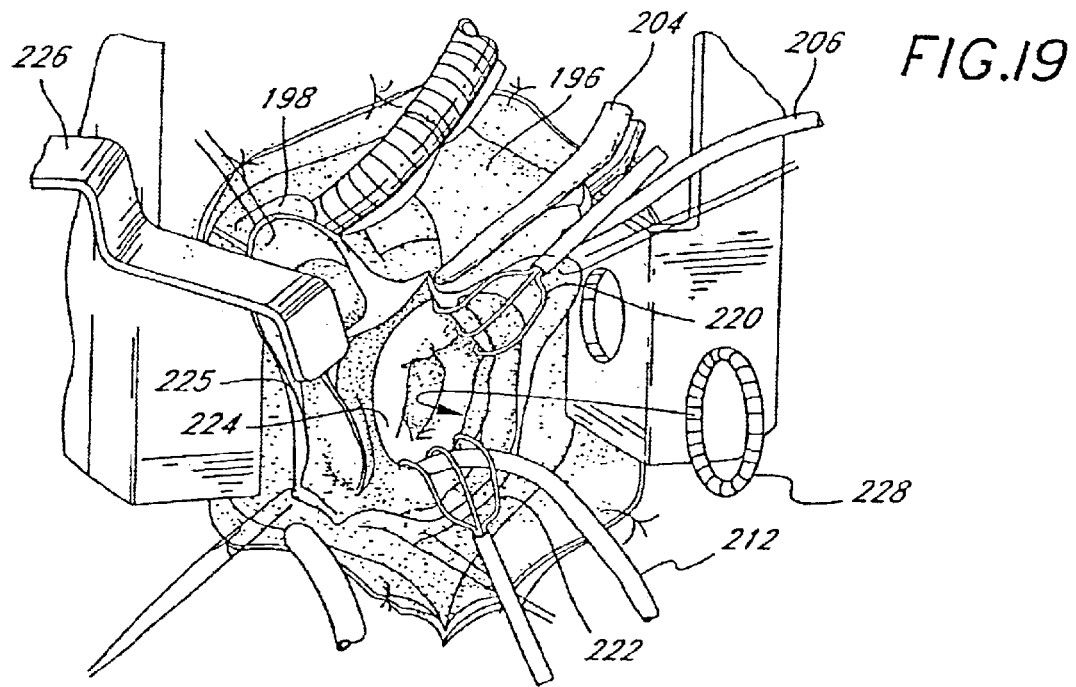
FIG. 19 is a pictorial illustration depicting an alternative way of exposing the surgical field of FIG. 17.

With reference to FIG. 19, hand-held refractors 220, 222 are then inserted into the superior and inferior portions of the left atrium, respectively, and used to pull the atrial tissue back and expose the mitral valve 224. Additionally, downward traction may be applied on the posterior lateral left atrial wall 225 to provide better exposure to the mitral valve 224. A deformable retractor 226, which may be manipulated into a shape that grasps the tissue but does not obstruct the surgical field, may be used to provide the downward traction on the posterior lateral left atrial wall 224. In addition, to further expose the surgical field, a flexible and resilient ring member 228 may be inserted into the field between the valve 224 and the left atrial wall. After the ring member is inserted, the ring 228 expands to facilitate lifting the tissue away from the valve area requiring surgery. The mitral valve 224 being fully exposed after achieving the above-described configuration, repair of the valve 224 may then be achieved using the devices of the present invention. By way of example only, the procedure for completing the surgical method after repair of a mitral valve is hereinafter described.

Figure 20:
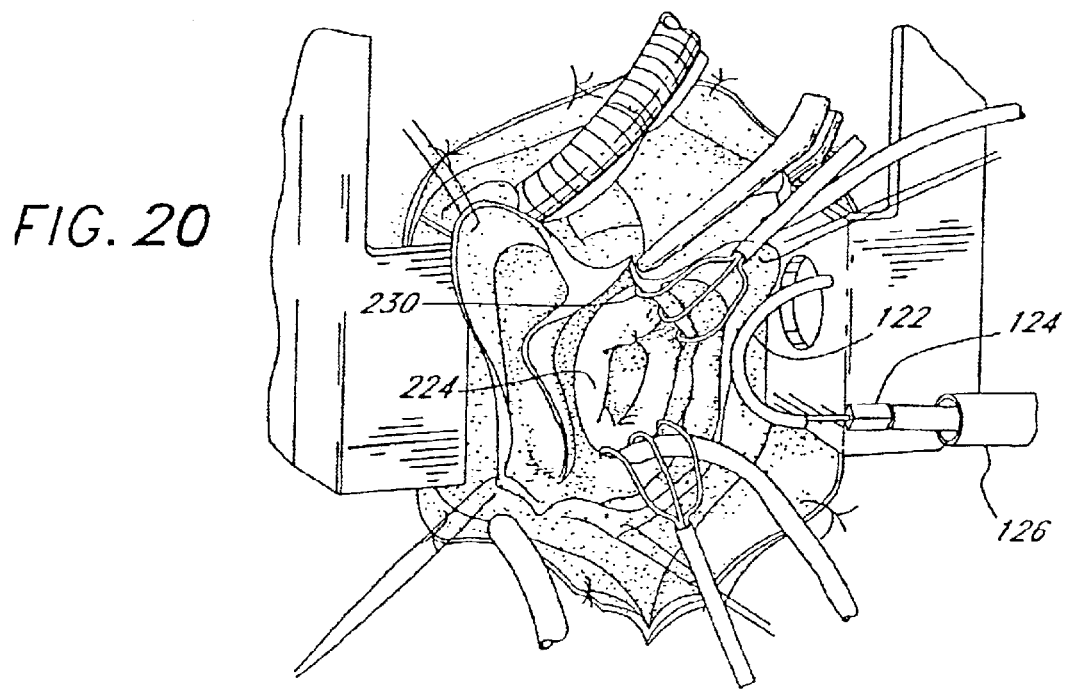
FIG. 20 is a pictorial illustration of the performance of an annuloplasty in the surgical field of FIG. 17.
Figure 21:
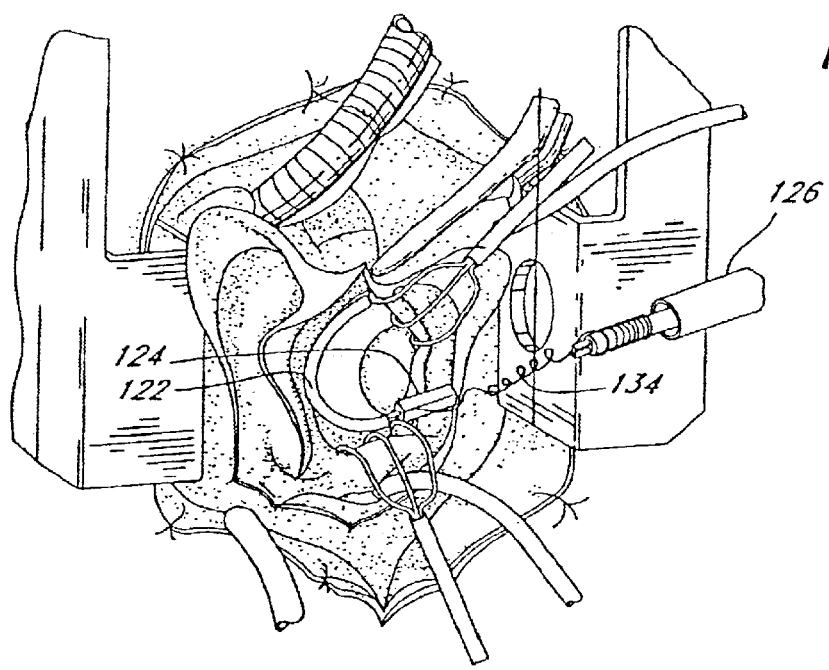
FIG. 21 is a pictorial illustration of the performance of an annuloplasty in the surgical field of FIG. 17.
Figure 22:
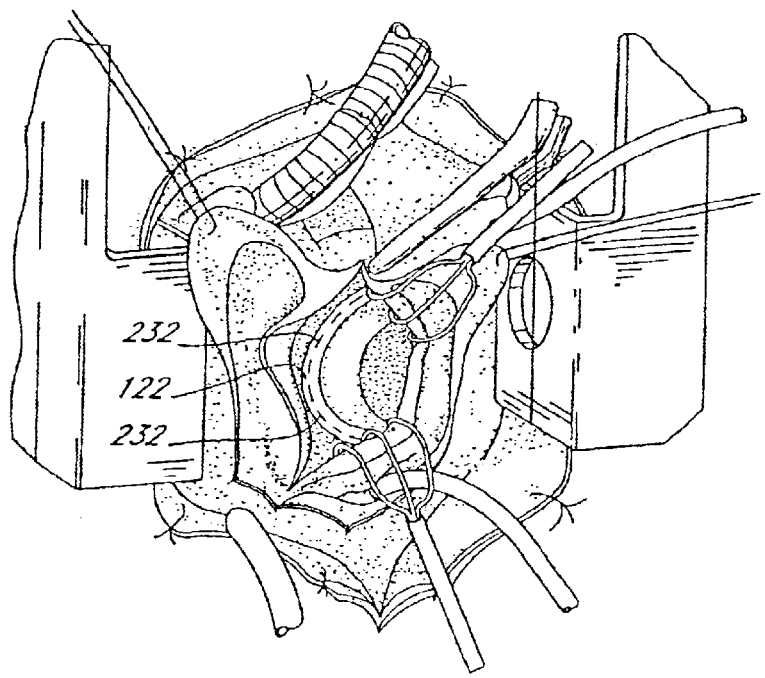
FIG. 22 is a pictorial illustration of the completion of an annuloplasty in the surgical field of FIG. 17.

Referring to FIGS. 20–22, after exposure of the mitral valve 224, an annuloplasty is performed. For example, the annuloplasty delivery system 120 of FIGS. 9–11 is introduced into the surgical field and the annuloplasty repair segment 122 attached to the template 124 is released into proximity of the annulus 230 from the delivery sheath 126. The tether 134 maintains a connection between the template 124 and delivery sheath 126 as the repair segment 122 is maneuvered and secured by sutures 232 into a corrective position in the annulus 230. Again, various implements are known for manipulating and suturing surgical devices in tight spaces, including robotically-assisted forceps and suture needles or stapling mechanisms, and will not be described or shown here. Finally, the template 124 is disengaged from the repair segment 122, and the annuloplasty delivery system 120 removed from the surgical site, as in FIG. 22.

The present invention thus provides an improved annuloplasty delivery system and/or holder that is especially suitable for minimally-invasive surgeries. The system enables delivery of an annuloplasty repair segment to the valve annulus through a tube, such as a catheter or cannula The system/holder includes a template to which the repair segment attaches that is capable of undergoing a shape change, either actively via a deflection mechanism or passively by virtue of instrinsic properties, such as a spring bias or material memory. The shape may be two- or three-dimensions, and typically forms a curve along at least a portion to conform around the annulus. The template is desirably an elongate member that assumes a generally linear shape for passing through the delivery tube, and then is actively or passively converted to the changed shape upon exiting from the distal end of the tube. The repair segment may be various lengths, from relatively short to almost a complete ring shape, and is flexible to assume the respective shapes of the template. The template may remain rigidly attached to a handle that extends from the proximal end of the tube, or may be released to enable free manipulation by the surgeon at the implantation site. A tether may be provided to maintain connection between the delivery tube and template while permitting maximum access and visibility around the repair segment during the attachment procedure. The template remains attached to the repair segment during the attachment procedure to support and maintain a desired shape of the repair segment. Once the repair segment is implanted, the template is detached, such as by severing connecting sutures, or by pulling it longitudinally from within the repair segment.

While the foregoing is a complete description of the preferred embodiments of the invention, various alternatives, modifications, and equivalents may be used. Moreover, it will be obvious that certain other modifications may be practiced within the scope of the appended claims.

What is claimed is:

1. A combination annuloplasty repair segment and holder, comprising:
   a holder including a template defining a distal end of the holder, the template being convertible from a generally linear shape to a curved shape that at least partly conforms to a corrected shape of an interior wall of a target annulus, wherein the template is biased toward the changed shape; and
   an annuloplasty repair segment attached to the template and convertible between the linear shape and the curved shape of the template.

2. The combination of claim 1, wherein the template is flexible and the shape change occurs from bending of the template.

3. The combination of claim 1, wherein the changed shape is a curve.

4. The combination of claim 1, wherein the curve is three-dimensional.

5. The combination of claim 1, further including a deflection mechanism for converting the template between the linear shape and the changed shape.

6. The combination of claim 1, wherein the template includes a plurality of hinged sections.

7. The combination of claim 6, further including a deflection mechanism for converting the template between the linear shape and the curved shape.

8. The combination of claim 1, wherein the template is capable of a temperature-induced shape change between the linear shape and the changed shape.

9. The combination of claim 1, wherein the template is flexible but unbiased from the linear shape, the holder further including a biasing member adapted to insert within the template so as to bias the template toward the curved shape.

10. The combination of claim 1, further including an elongate shaft located proximally with respect and attached to the template for manipulating the template to position the annuloplasty repair segment into proximity with a valve annulus.

11. The combination of claim 10, wherein the shaft is rigid.

12. The combination of claim 1, further including an anchor mandrel to which the template is releasably attached, and a tether connecting the template and anchor mandrel when released.

13. The combination of claim 1, further including suture location markers on the template to facilitate suture alignment with anatomical landmarks.

* * * * *